(12) United States Patent  (10) Patent No.: US 7,853,057 B2
Matsumoto  (45) Date of Patent: Dec. 14, 2010

(54) IMAGE PROCESSING METHOD AND DEVICE USING A VIRTUAL RAY AND VECTOR INFORMATION

(75) Inventor: Kazuhiko Matsumoto, Minato-ku (JP)

(73) Assignee: Ziosoft, Inc., Tokyo (JP)

( * ) Notice: Subject to any disclaimer, the term of this patent is extended or adjusted under 35 U.S.C. 154(b) by 1063 days.

(21) Appl. No.: 11/346,058

(22) Filed: Feb. 2, 2006

(65) Prior Publication Data

US 2006/0193510 A1 Aug. 31, 2006

(30) Foreign Application Priority Data

Feb. 28, 2005 (JP) .............................. 2005-054863

(51) Int. Cl.
*G06K 9/00* (2006.01)
(52) U.S. Cl. ....................... 382/128; 382/154
(58) Field of Classification Search ................. 382/128, 382/154, 130; 345/424
See application file for complete search history.

(56) References Cited

U.S. PATENT DOCUMENTS

| 6,072,497 A | 6/2000 | Litchtenbelt et al. |
| 6,205,350 B1 | 3/2001 | Lorenz et al. |
| 6,480,732 B1 * | 11/2002 | Tanaka et al. ............... 600/425 |
| 6,654,012 B1 | 11/2003 | Lauer et al. |
| 2003/0053697 A1 * | 3/2003 | Aylward et al. ............. 382/203 |
| 2004/0197015 A1 * | 10/2004 | Fan et al. ..................... 382/128 |

FOREIGN PATENT DOCUMENTS

| DE | 100 12 172 A1 | 9/2001 |
| DE | 100 12 174 | 9/2001 |

OTHER PUBLICATIONS van Dam, "Raytracing Basics", Introduction to Computer Graphics, Oct. 2001, pp. 1-39 (Cited in GOA, English Text).
Schmittler et al., "SaarCOR-A Hardware Architecture for Ray Tracing", Computer Graphics Group, Saarland University, Germany, 2002, pp. 1-11 (Cited in GOA, English Text).

* cited by examiner

*Primary Examiner*—Bhavesh M Mehta
*Assistant Examiner*—Hadi Akhavannik
(74) *Attorney, Agent, or Firm*—Pearne & Gordon LLP

(57) ABSTRACT

A threshold value T which is a little larger than voxel values of a target tissue such as bloodstream is determined. Next, a virtual ray is projected, and voxel values on the virtual ray are obtained as an array A1 (original array). Then, an array A2 (replaced array) is generated by the voxel values of the array A1 which are equal to or larger than the threshold value T are flipped-over at the threshold value T. Then, a part of the data on the array A2, e.g., flipped-over data corresponding to the center part of the calcified region is excluded. Next, a maximum value M2 on the array A2 is obtained, and a value M1 on the array A1 corresponding to the value M2 is obtained. Then, the value M1 is employed as a pixel value for the virtual ray.

20 Claims, 33 Drawing Sheets

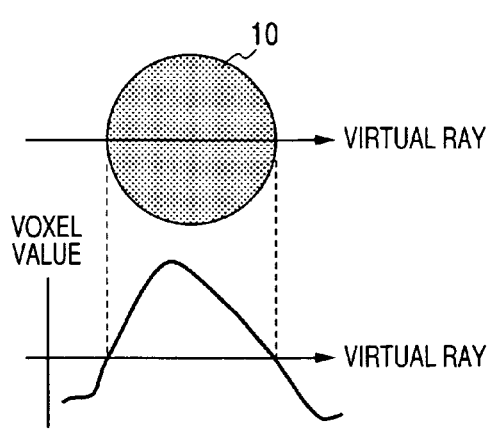 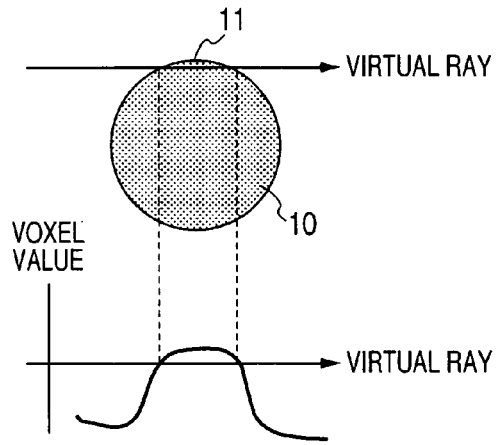
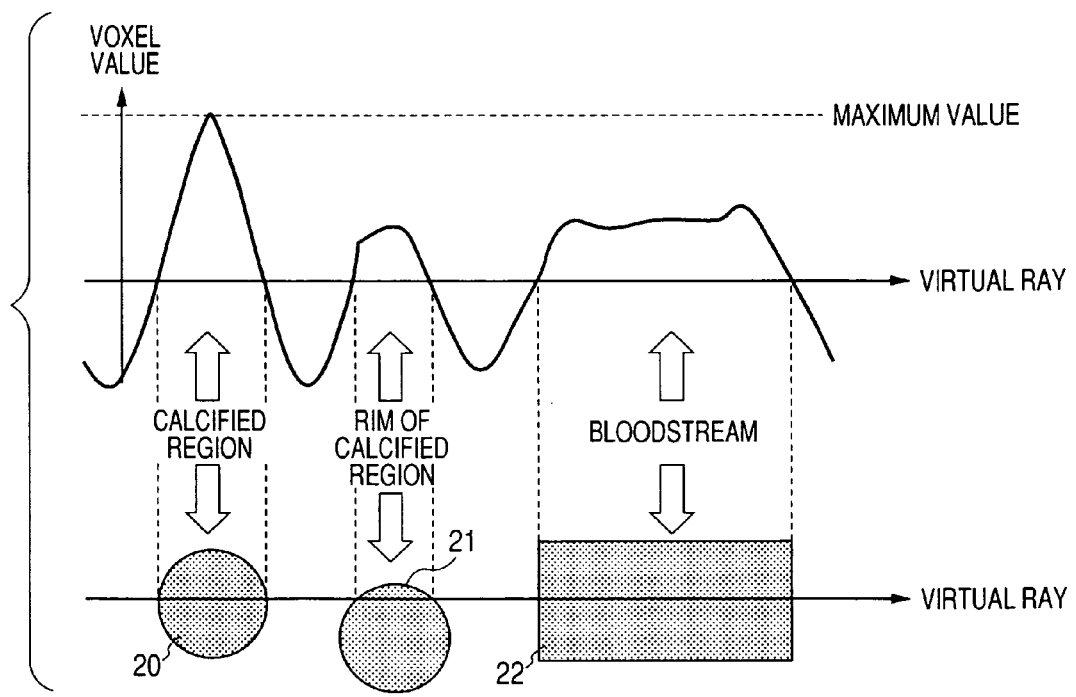

MODIFICATION OF PROFILE
PATTERN WITH GRADIENT FACTOR

FIRST PROFILE PATTERN

MODIFICATION OF FILE PATTERN WITH FLIP-OVER

SECOND PROFILE PATTERN

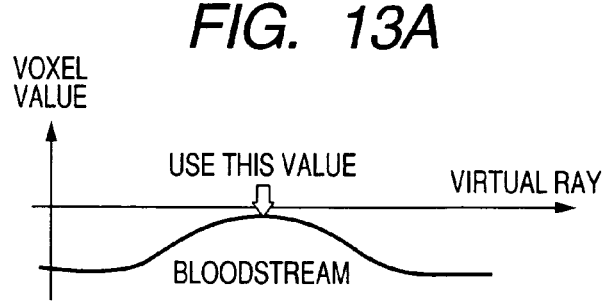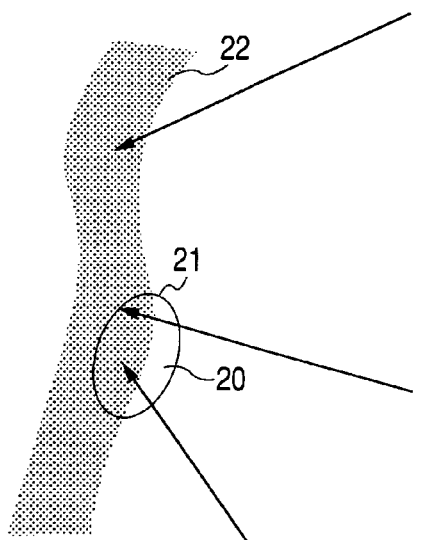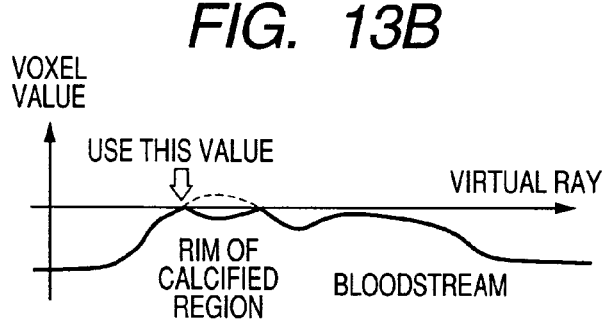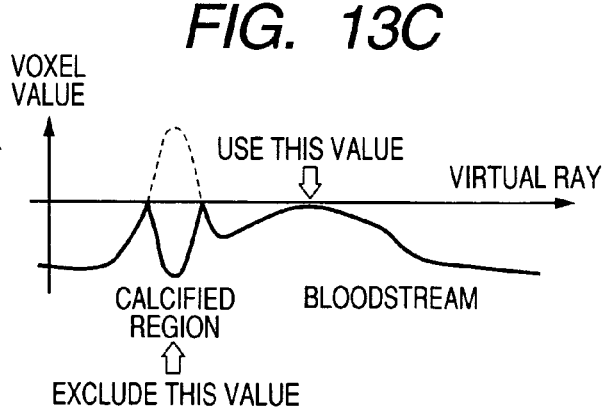

IT IS NOT POSSIBLE TO DETERMINE
WHETHER BLOODSTREAM REMAINS DUE
TO CALCIFIED REGION BEING AS OBSTACLE

BLOODSTREAM　　BLOODSTREAM
IS STOPPED　　　　REMAINS

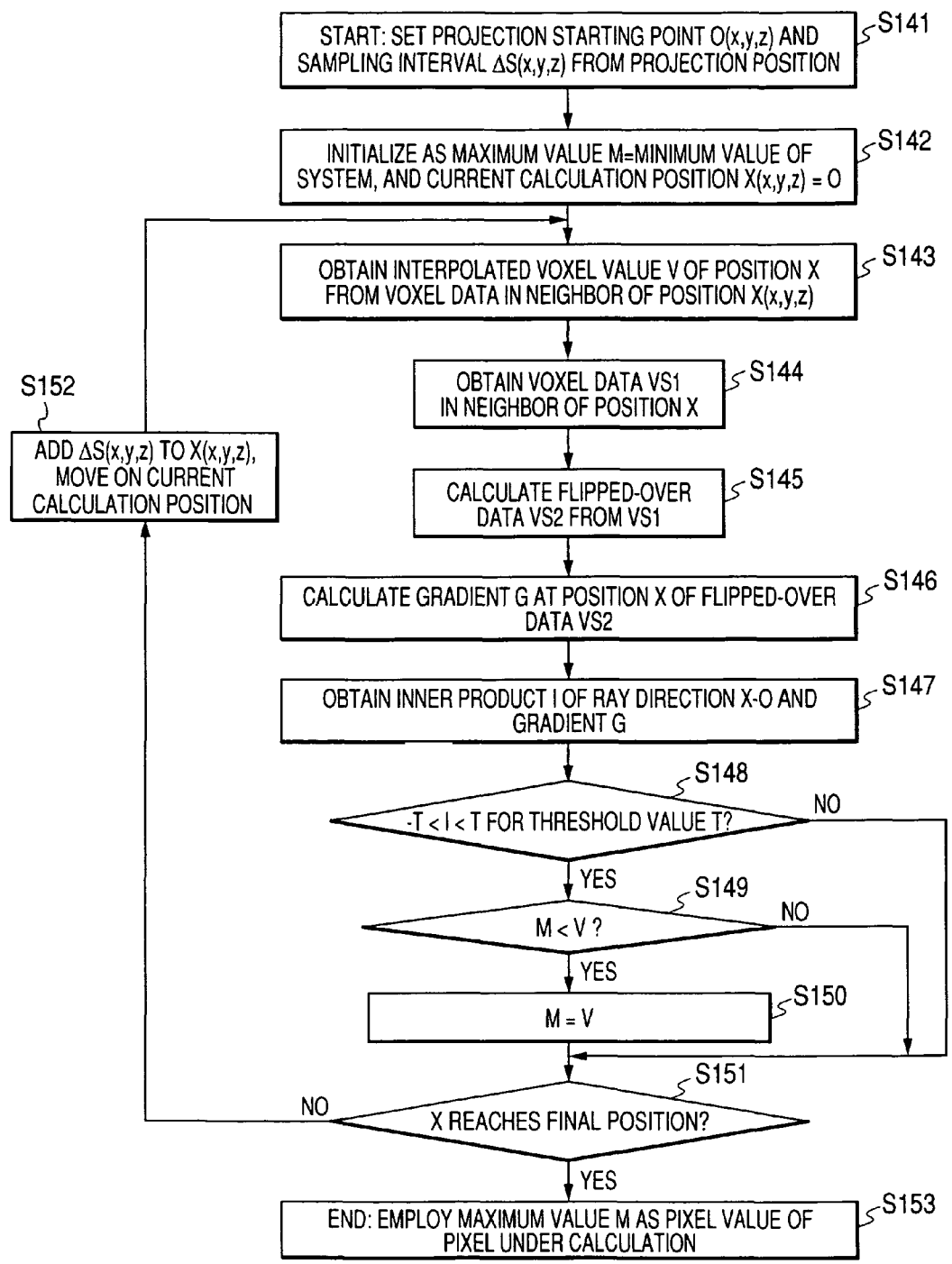

FIG. 30A
FIG. 30B
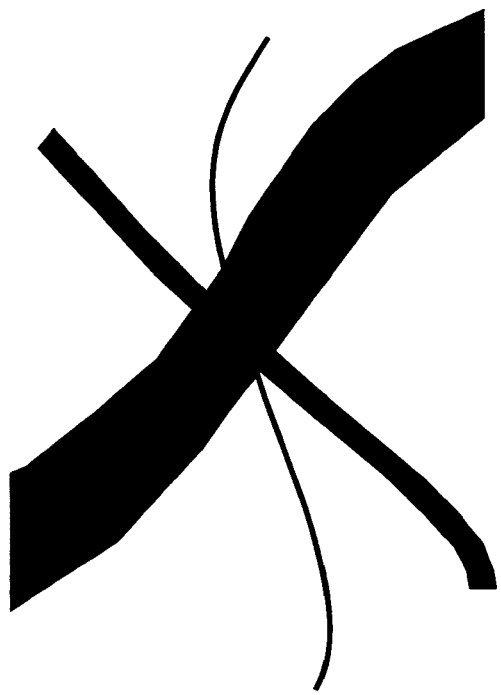
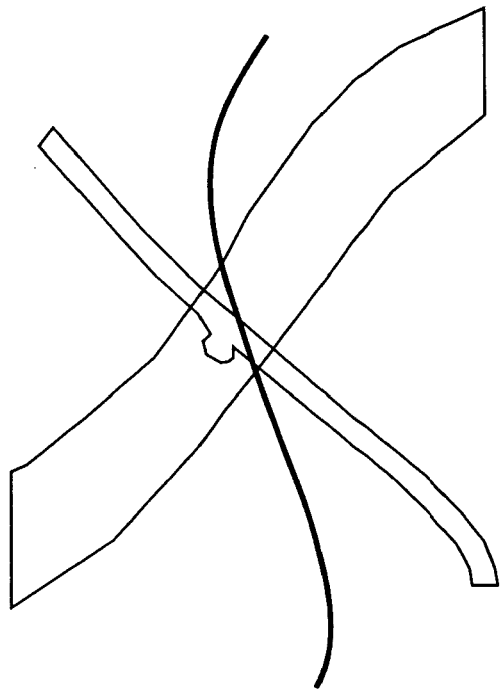

US 7,853,057 B2

IMAGE PROCESSING METHOD AND DEVICE USING A VIRTUAL RAY AND VECTOR INFORMATION

This application claims foreign priority based on Japanese Patent application No. 2005-054863, filed Feb. 28, 2005, the contents of which is incorporated herein by reference in its entirety.

BACKGROUND OF THE INVENTION

1. Field of the Invention

The present invention relates to an image processing method and image processing device by volume rendering.

2. Description of the Related Art

Hitherto, a projected image has been acquired by projecting virtual ray into a three-dimensional image obtained with a computed tomography (CT) apparatus, a magnetic resonance imaging (MRI) apparatus, or the like. As a processing for obtaining such a projected image, volume rendering has been widely employed. As the volume rendering, there are known, for example, MIP (Maximum Intensity Projection) processing wherein maximum voxel values are extracted in a projecting direction and are projected, MinIP (Minimum Intensity Projection) processing wherein minimum voxel values are extracted and projected, a ray casting method wherein a virtual ray is projected in a projecting direction and a reflected light from an object is calculated, etc.

FIGS. 31A to 31D are explanatory drawings of the MIP processing, and show a relationship between 3D (three-dimensional) data corresponding to voxel values of a rendering object and maximum values selected as data for display. In the MIP processing, since a maximum value of the 3D data on the projection line shown by an arrow in each figure is used as the display data, 4, 8, 8, and 8, each of which are maximum values of the 3D data, are used as the display data in FIGS. 31A, 31B, 31C, and 31D, respectively.

FIG. 32A shows a Raycast image, and FIG. 32B shows an MIP image. The Raycast image shown in FIG. 32A is one kind of volume rendering image, and pixels are determined by accumulating reflected light-s from a plurality of voxels on a virtual ray. Therefore, it is effective in rendering of outlines and a graphical image is obtained. Moreover, in the case that the virtual ray passes between voxel data, calculation may be conducted based on not the voxel data themselves but information obtained by interpolating the voxel data.

On the other hand, the MIP image shown in FIG. 32B is effective in objectivity and a high speed calculation is possible, since, as mentioned above, the pixels are determined by selecting a single voxel on a virtual ray and the voxel values are rendered as they are. Therefore, the MIP images are frequently used in the rendering of blood vessels. Sometimes interpolated voxel values are used in MIP processing, and a plurality of voxels are referred to, but there is no difference in the fact that only the information on a single point on the virtual ray is used. However, sometimes it becomes difficult to render an organ having no characteristic in the voxel values.

FIGS. 33A and 33B are drawings for illustrating the situation, in an MIP image, of a portion where a bloodstream 52 is obstructed by a calcified region 50 attached inside a blood vessel. Moreover, FIGS. 33A and 33B show the cases that the same portion of the blood vessel is observed in the directions 90 degrees different from each other.

In the MIP image shown in FIG. 33A, a size of the calcified region 50 having a high CT value in the blood vessel can be ascertained. However, the bloodstream 52 in a stenotic portion 51 obstructed with the calcified region 50 cannot be measured correctly in some cases. Moreover, in the MIP image shown in FIG. 33B, the observation of the bloodstream 52 becomes difficult since the calcified region 50 becomes an obstacle. The bloodstream 52 cannot be observed even when the bloodstream 52 actually positions at the back of or in front of the calcified region 50.

FIG. 34 is a drawing for explaining characteristics of voxel values profile along a virtual ray, showing a change in voxel values on the virtual ray at the portion where a calcified region having a high CT value exists in a blood vessel. On the virtual ray, the voxel values corresponding to the calcified region have large values and show sharp-peaked values. On the other hand, the voxel values of the bloodstream have small values and show smooth-shaped values.

Therefore, in the MIP image, since the maximum value of the voxel values on the virtual ray is directly displayed, when a blood vessel having a calcified region is observed, the calcified region with a large voxel value is displayed, and thus the bloodstream positions at the back of or in front of the calcified region cannot be displayed.

FIG. 35 is a drawing for illustrating a solution of the related art when the bloodstream positioning at the back of or in front of the calcified region is observed in the MIP image. As shown in FIG. 35, replaced volume data is generated by replacing the CT values of the calcified region with some values (e.g., volume data of air). Accordingly, the voxel values corresponding to the calcified region are lowered so as to display the bloodstream. Alternatively, substantially the same effect is obtained by removing a region corresponding to the calcified region from the rendering object. However, in the above two methods, it is necessary to perform a region extraction processing to specify the calcified region in advance.

That is, in the solution of the related art, at the pre-stage of the volume rendering, a calcified region is detected using a region extraction method with a threshold value or other algorithms. Then, using the result of the region extraction, the volume data is modified (the calcified region is removed) or mask data is generated (non-rendering region is designated using mask volume) to enable the display of the bloodstream.

FIG. 36 is a flow chart showing calculation of each pixel on the screen in a ray casting method of the related art. In the ray casting method, the following calculation is performed for all the pixels on the screen. First, from the projection position, a projection starting point $\underline{O}(x,y,z)$ and a sampling interval $\Delta S(x,y,z)$ are set (Step S201).

Next, a reflecting light E is initialized as "0", a remaining light I as "1", and a current calculation position $X(x,y,z)$ as "$\underline{O}$" (Step S 202). Then, from voxel data in the neighbor of the position $X(x,y,z)$, an interpolated voxel value V of the position X is obtained (Step S203). In addition, an opacity α corresponding to the interpolated voxel value V is obtained (Step S204) In this case, a function of $\alpha=f(V)$ is prepared beforehand (Step S 212).

Next, a color value C corresponding to the interpolated voxel value V is obtained (Step S205). Then, from voxel data in the neighbor of the position $X(x,y,z)$, a gradient G of the position X is obtained, and from a ray direction X–$\underline{O}$ and the gradient G, a shading coefficient β is obtained (Step S206).

Next, an attenuated light D ($D=I*\alpha$) and partial reflecting light F ($F=\beta*D*C$) at the position $X(x,y,z)$ are calculated (Step S207). Then, the reflecting light E and the remaining light I are updated (I=I–D, E=E+F) (Step S208).

Next, it is determined whether or not X reaches a final position, and whether or not the remaining light I is "0" (Step S209). When X is not the final position and the remaining light I is not "0" (no), $\Delta S(x,y,z)$ is added to $X(x,y,z)$, the current calculation position is moved on (Step S210), and the processes of and after Step S203 are repeated. On the other hand, when X reaches the final position or the remaining light I is "0" (yes), calculation is finished with the reflecting light E being used as the pixel value of the pixel under calculation (Step 211).

FIG. 37 shows a flow chart for calculating each pixel on the screen in an MIP processing of the related art. In the MIP processing, the following calculation is performed for all the pixels on the screen. First, from the projection position, a projection starting point O(x,y,z) and a sampling interval ΔS(x,y,z) are set (Step S221).

Next, a maximum value M is initialized as a minimum value of the system and a current calculation position X(x,y,z) as "O" (Step S 222). Then, from voxel data in the neighbor of the position X(x,y,z), a interpolated voxel value V of the position X is obtained (Step S223).

Next, the maximum value M and the interpolated voxel value V are compared (Step S224). When the maximum value M is smaller than the interpolated voxel value V (yes), the interpolated voxel value V is assigned to the maximum value M as a new Maximum value (Step S225). Then, it is determined whether or not the current calculation position X reaches a final position (Step 226). When the current calculation position X is at the final position (no), ΔS(x,y,z) is added to X(x,y,z), the current calculation position is moved on (Step S227), and the processes of and after Step S223 are repeated. On the other hand, when the current calculation position X reaches the final position (yes), the maximum value M is used as the pixel value of the pixel under calculation (Step 228).

Moreover, in U.S. Pat. No. 6,205,350, second volume data not containing an obstructing region is generated, the maximum value in the second volume data is obtained, and a value in the original volume data at the position corresponding to the position of the maximum value is used for rendering.

However, in the above methods of the related art, obstructing regions such as calcified regions are removed by the replacement of volume data. Hence the information of the obstructing regions themselves is completely lost. Moreover, it is difficult to exclude exactly only the obstructing region and to render the bloodstream correctly. Furthermore, since an extracted region is designated in voxel units, aliases may arise at the boundary of the region, which results in deterioration of the image. In addition, retention of mask information and second volume data may cause an unnecessary load to the memory, and when the volume data is modified, the comparison with the original date becomes difficult. Additionally, the extraction of individual obstructing regions takes much time and largely depends on subjective factors of a user. In particular, since the extraction depends on the subjective factors of the user, reproducibility by each user is low, which results in lack of universality as objective diagnostic information. Therefore, there is a problem that it is difficult to use the methods at actual diagnosis and hence actually, they are not so widely employed.

FIGS. 38A, 38B and 38C are drawings for illustrating the problems in the MIP image of the related art. In the method of the related art, as shown in FIGS. 38A and 38B, a calcified region 61 is removed in order to observe a bloodstream 60 at the back of and in front of the calcified region 61. In that case, a portion 62 where the bloodstream 60 exists is also removed. Moreover, in the method of the related art, the calcified region 61 is not displayed at all, and hence it becomes difficult to determine a diseased part. Also a necessary region is removed frequently, and hence reliability decreases.

In this case, as shown in FIG. 38C, information of a portion 63 which is an imprint of the removed calcified region is necessary. Particularly, information of an outline portion 64 of the calcified region is required. That is, when only the outline of the calcified region is displayed without displaying the filling of the calcified region, the display is effective for diagnosis.

In this regard, since the calcified region is a three-dimensional region, the boundary surface of the region constitutes a curved surface in a three-dimensional space. Therefore, when the calcification is rendered by a mask application or a volume modification of the related art, each pixel of an image represents an intersection of a virtual ray and the three-dimensional boundary surface, the intersection constituting the pixel, so that a two-dimensional outline cannot be represented. On the other hand, when diagnosis is conducted while viewing the image, for the calculation of images, information of the two-dimensional outline portion of the calcified region and the neighbor of the calcified region, particularly at the back of and in front of the calcified region is necessary. With regard to the two-dimensional outline portion, when only the portion can be rendered where the virtual ray grazes the rim of the calcified region three-dimensionally, the rendering is effective for diagnosis.

SUMMARY OF THE INVENTION

An object of the invention is to provide an image processing method and image processing device in which a rendering is possible by determining a two-dimensional outline of an obstructing region dynamically, while removing the obstructing region such as a calcified region, when calculation such as MIP processing is performed for a medical image.

An image processing method of the invention is an image processing method by volume rendering, comprising: selecting at least one point which is aligned on a virtual ray; and determining a pixel value of an image by the volume rendering based on each value of the selected at least one point, wherein said at least one point is selected based on a first vector information and a second vector information, and positional relationship of said at least one point is mutually exchangeable on the virtual ray in determining the pixel value. In the related art, in the volume rendering method without calculating a reflecting light, such as MIP method, vector information is not used. However, according to the above configuration, by using the vector information, for example, a two-dimensional effect (two-dimensional outline) depending on the direction of the virtual ray can be added to the image. Thereby, it becomes possible to observe, for example, shape information of an obstructing region and information of the neighbor thereof at one time, utilizing the two-dimensional outline.

The processing object of the image processing method of the invention is volume rendering. In the above expression "positional relationship of at least one point is mutually exchangeable on the virtual ray", "point" is used instead of "voxel" because, in many cases, pixel values are calculated based not on voxel values but on values obtained by interpolating the voxel values. Furthermore, in the expression, "at least one point" is used instead of "one point" because the invention can be applied not only to MIP method where only one point on a virtual ray is used, but also to other methods such as Top10MIP method, in which an average value of top ten points on a virtual ray is displayed. The MIP method is included in an image processing method of the present invention, since even when volume data is inversed in a direction of depth, the same image is obtained. In the MIP method and the like, since the positional relationship of points on the virtual ray is not used, a value such as opacity cannot be defined. This situation is the same in an average value method which uses an average value of points on a virtual ray, since even when the positions of the points are mutually exchanged, the result is not affected. Also in a method using a weighted average of points on a virtual ray, even when the positions of the points are mutually exchanged along with their associated weights (or degree of contribution of each point on a pixel), the result is not affected. Accordingly, in an image processing method in the present invention, the degree of contribution may be multi-valued. In a volume rendering method to which the present invention is applicable, gradient of a voxel is hitherto not considered in computation, since such method is not based on a simulation of a light ray. To the contrary, in ray casting method, opacity is associated with each voxel and attenuation of light amount of a virtual ray passing through voxels is processed. Accordingly, a different image is obtained when back and front of the volume data are inverted.

Moreover, the first vector information is mainly a direction vector of the virtual ray, but when other direction vector is used, an image corresponding to the other direction vector is obtained. On the other hand, the second vector information is mainly a gradient of voxel (including interpolated gradient), but other vector information related to voxels, such as movement information, can be used.

Moreover, in the image processing method of the invention, the first vector information is a direction vector of the virtual ray. In the image processing method of the invention, the second vector information is gradient information. In the image processing method of the invention, a number of the selected point is one.

In the image processing method of the invention, said at least one point is selected further based on data obtained by replacing original data on the virtual ray. In the image processing method of the invention, values of the replaced data are obtained by flipping values of the original data over at a threshold value.

In the image processing method of the invention, said at least one point is selected further based on a magnitude of the second vector information. In the image processing method of the invention, said at least one point is selected further based on an angle between the first vector information and the second vector information. The image processing method of the invention further comprises displaying a two-dimensional outline of a region included in a rendering object on the volume rendering image.

Further an image processing method of the invention is an image processing method by volume rendering, comprising: selecting at least one point which is aligned on a virtual ray; determining a degree of contribution of each value of the selected at least one point; and determining a pixel value of an image by the volume rendering based on the determined degree of contribution and said each value of the selected at least one point.

In the volume rendering method of the related art, the degree of contribution on the processing for determining pixel values is provided through mask information or the like. Thus, the degree of contribution is three-dimensionally determined and a two-dimensional effect cannot be added. To the contrary, according to the above configuration, since the degree of contribution is determined on the virtual ray, the two-dimensional effect can be added to the image.

Moreover, in the image processing method of the invention, at least one of the degree of contribution is zero. In the image processing method of the invention, the degree of contribution is determined based on data obtained by replacing original data on the virtual ray. In the image processing method of the invention, values of the replaced data are obtained by flipping values of the original data over at a threshold value.

Furthermore, in the image processing method of the invention, the degree of contribution is determined further based on a gradient vector which is on a volume and corresponds to a position of the selected point, and a direction vector of the virtual ray. In the image processing method of the invention, the degree of contribution is determined further based on a change of voxel values on the virtual ray.

In addition, the image processing method of the invention further comprises displaying a two-dimensional outline of a region included in a rendering object on the volume rendering image, based on the determined pixel value. The image processing method of the invention further comprises displaying excluding a region included in a rendering object on the volume rendering image.

Moreover, in the image processing method of the invention, the volume rendering image and an another image are displayed arranged in side by side, being overlapped with each other, or by showing a difference of the images. In the image processing method of the invention, the pixel value is determined only for a region which is designated by a user. In the image processing method of the invention, the pixel value is determined only for a window provided on a screen.

Furthermore, in the image processing method of the invention, the outline is displayed while continuously changed. In the image processing method of the invention, the image processing is performed by parallel processing. In the image processing method of the invention, the image processing is performed by a GPU (graphics processing unit). In the image processing method of the invention, the image processing is performed by a GUI (graphical user interface) in which parameters are changeable.

In addition, in the image processing method of the invention, the image processing is performed by MIP (Maximum Intensity Projection) method, MinIP (Minimum Intensity Projection) method, Raysum method or an average value method. In the image processing method of the invention, the image processing is performed by MIP (Maximum Intensity Projection) method, MinIP (Minimum Intensity Projection) method, Raysum method, an average value method or ray casting method. The image processing method of the present invention further comprises displaying the selected at least one point on a sectional image of a rendering object, said sectional image including the virtual ray.

Furthermore, an image processing device in the invention is an image processing device for displaying a volume rendering image, being operative to: select at least one point which is aligned on a virtual ray; determine a pixel value of an image by the volume rendering based on each value of the selected at least one point; and display a two-dimensional outline of a region included in a rendering object on the volume rendering image, wherein positional relationship of said at least one point is mutually exchangeable on the virtual ray in determining the pixel value.

According to the image processing method of the invention, at the time when a virtual ray is projected, a diagnostic object can be accurately displayed by determining parts of voxel data in the voxel data on the virtual ray, e.g., a two-dimensional center part of an obstructing region, as nondisplay data, and determining a two-dimensional outline of the obstructing region as display data.

BRIEF DESCRIPTION OF THE DRAWINGS

FIGS. 1A and 1B are drawings for explaining characteristics of voxel values profile along a virtual ray used in the image processing method according to embodiments of the invention.

FIG. 2 is a drawing for explaining characteristics of voxel values profile along a virtual ray, showing changes of voxel values when the virtual ray passes through the center part of a calcified region 20, rim of the calcified region 21, and a bloodstream 22.

FIGS. 13A to 13C are drawings for explaining characteristics of voxel values profile along a virtual ray, showing profile patterns (1) obtained by the image processing method according to a third embodiment of the invention.

FIG. 13D shows an image displayed by the image processing method according to a third embodiment of the invention.

FIG. 29 shows a flow chart of MIP processing in which gradient processing and flip-over processing are conducted in the image processing method according to a ninth embodiment of the invention.

FIGS. 30A and 30B are explanatory drawings of the case when the crossing of bloodstreams are visualized.

DESCRIPTION OF THE PREFERRED EMBODIMENTS

Figure 3:
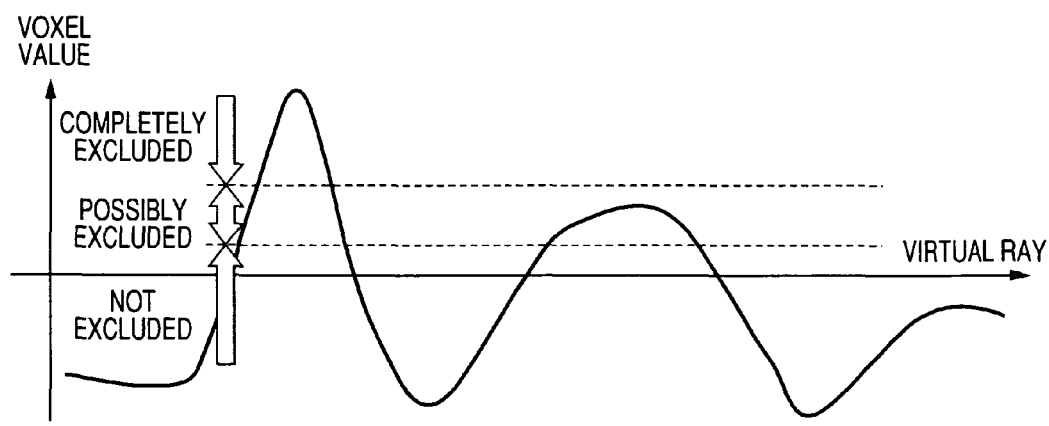
FIG. 3 is a drawing for explaining characteristics of voxel values profile along a virtual ray, showing the case when gradient is used in the MIP processing (without flip-over) in the image processing according to a first embodiment of the embodiment.

FIGS. 1A and 1B show a change (profile pattern) of voxel values (including interpolated voxel values) on a virtual ray when the virtual ray passes through volume data in the image processing method of the present embodiments. The profile pattern is determined with every virtual ray, and has a characteristic for each object through which the virtual ray passes. Here, a profile pattern is shown of the voxel values when the virtual ray passes through an obstructing region such as a calcified region. When the virtual ray passes through the center part of the obstructing region 10 as shown in FIG. 1A, the voxel values corresponding to the obstructing region 10 jump remarkably. On the other hand, when the virtual ray grazes the rim 11 of the obstructing region 10 as shown in FIG. 1B, increase of the voxel values corresponding to the obstructing region 10 is limiting and relatively flat.

FIG. 2 shows a profile pattern of voxel values when a virtual ray passes through the center part and a rim 21 of a calcified region 20, and a bloodstream 22. When the virtual ray passes through the center part of the calcified region 20, the voxel values have a high peak (maximum value). When the virtual ray passes through the rim 21 of the calcified region 20, the voxel values have a low peak. Moreover, the voxel values corresponding to the bloodstream 22 have a flat hill-like pattern.

First Embodiment (MIP Processing—Gradient is Used without Flip-Over)

FIG. 3 is an explanatory drawing of the case when gradient is used in the MIP processing (without flip-over) in the image processing of the present embodiment. In the present embodiment, two threshold values are prepared, and voxel values are separated into three groups by the threshold values in order to perform calculation for exclusion of an obstructing region. That is, the voxel values are separated into three groups: a group to be completely excluded (a portion having sufficiently high voxel values is regarded as a calcified region and removed); a group to be possibly excluded (a region where voxel values do not give sufficient clues for determining whether the region should be removed or not); and a group not to be excluded (normal tissue). Then only the region in the group to be possibly excluded is separated again based on the gradient.

In the present embodiment, both of the calcified region itself and the two-dimensional outline of the calcified region can be determined by using the direction vector of the virtual ray and the gradient information of voxels through which the virtual ray passes. The gradient information of the voxels can be obtained by acquiring the difference of neighboring 3×3×3 voxel region of a target voxel.

On the other hand, in the related art, voxel values having equal to or larger than a certain threshold value are automatically removed, and hence the maximum value on the virtual ray is necessarily fixed to the threshold value. In that case, the bloodstream or the like existing at the back of or in front of the calcified region can not be observed. In the present embodiment, an intermediate range of voxel value is provided, and for a voxel having value in the intermediate range, whether the voxel belongs to the calcified region or not is determined by using the gradient, whereby a maximum value of a desired portion is obtained.

Figure 4A:
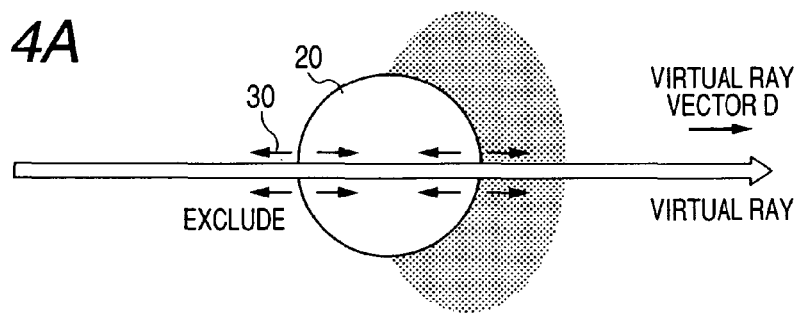
FIGS. 4A and 4B are explanatory drawings of a determining method (1) whether voxel values corresponding to the virtual ray are excluded in the image processing method according to a first embodiment of the invention.
Figure 4B:
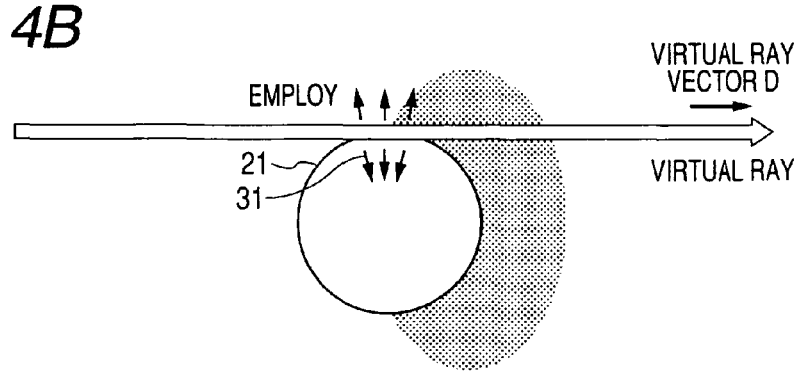

FIGS. 4A and 4B are explanatory drawings of a determining method (1) whether voxel values corresponding to the virtual ray are excluded in the image processing method of the present embodiment. In this case, a gradient vector G of three-dimensional voxel values is used as a determination method for excluding the center part of a calcified region and employing only the rim of the calcified region.

As shown in FIG. 4A, when the virtual ray passes through the center part of the calcified region 20, the gradient vector G 30 of the voxel becomes substantially parallel to the advancing direction of the virtual ray. Therefore, the portion where the gradient vector G 30 is substantially parallel to the advancing direction of the virtual ray is determined to be the center part of the calcified region 20, and thus the portion is excluded from display data.

On the other hand, as shown in FIG. 4B, when the virtual ray grazes the rim 21 of the calcified region, the gradient vector G 31 of the voxel becomes substantially perpendicular to the advancing direction of the virtual ray. Therefore, the portion where the gradient vector G 31 is substantially perpendicular to the advancing direction of the virtual ray is determined to be the rim 21 of the calcified region, and thus the portion is employed as display data.

In this case, determination for excluding or employing the display data can be conducted as follows: an inner product |D·G| is obtained by a virtual ray vector D and the gradient vector G in a candidate position of the maximum value of the voxel values; then, the absolute value |D·G| is compared with a threshold value of permissible parallelism TP (to be precisely described in FIG. 24). Moreover, the threshold value of permissible parallelism TP can be dynamically changed through GUI (Graphical User Interface) by a user, and the degree of removal of the calcified region can be changed while viewing the displayed image.

Figure 5A:
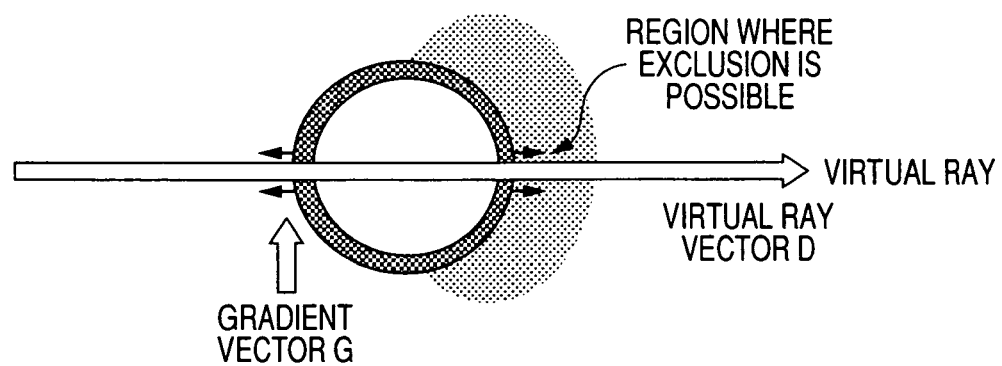
FIGS. 5A and 5B are explanatory drawings of the case when whether voxel values corresponding to the virtual ray are excluded from the display data is determined for the region in the group to be possibly excluded in an image processing method according to a first embodiment of the invention.
Figure 5B:
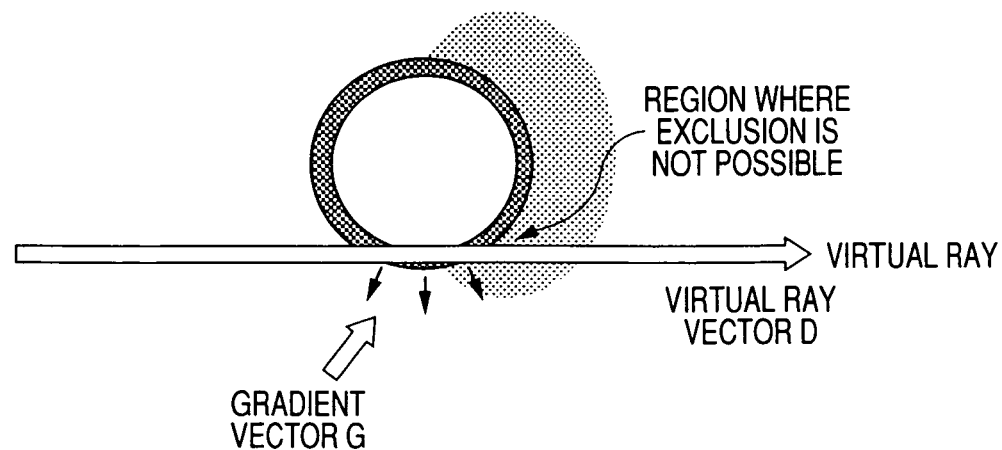

FIGS. 5A and 5B are explanatory drawings of the case when whether voxel values corresponding to the virtual ray are excluded from the display data is determined for the region in the group to be possibly excluded, in an image processing method of the present embodiment. FIG. 5A shows the case when the virtual ray passes through the center part of the obstructing region. FIG. 5B shows the case when the virtual ray passes through the outline of the obstructing region. The determination whether the exclusion is possible for the region in the group to be possibly excluded is performed by using an evaluation function f using the gradient vector G and a virtual ray vector D. That is, when the following conditional expression:

$$f(G,D) > \text{a threshold value}$$

is satisfied, it is determined that the exclusion is possible. For example, the expression may be:

$$f(G,D)=(1-(1-G\cdot D/(|G|\cdot|D|)))^{\wedge}2*h(51\ G|))\ (G\cdot D\text{ is inner product of vector }G\text{ and }D)$$

wherein $1-(1-G\cdot D/(|G|\cdot|D|))$ is a value relating to an intersecting angle of the gradient vector G and the virtual ray vector D, and $h(|G|)$ is a normalized value of the gradient vector G.

Figure 6:
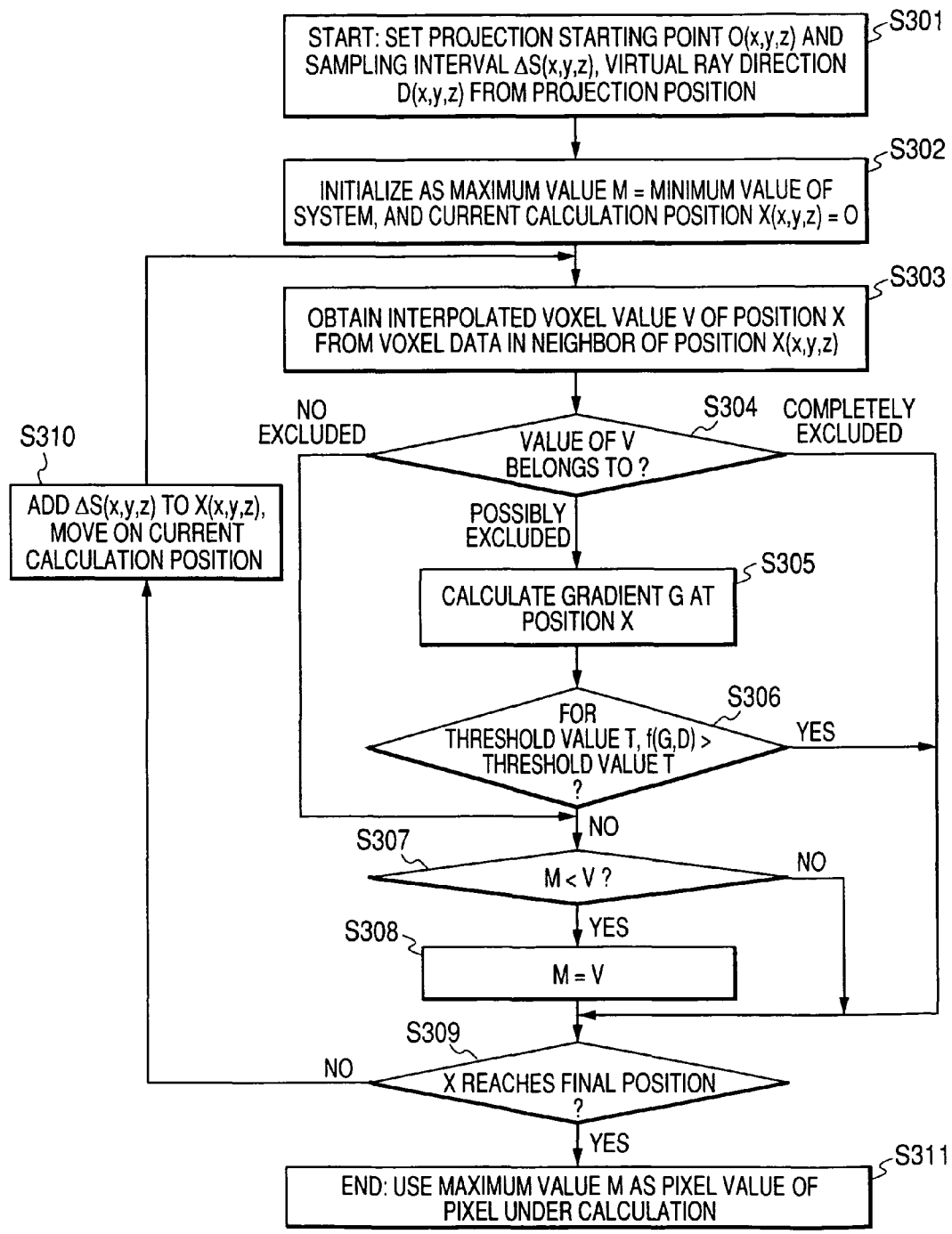
FIG. 6 is a flow chart of MIP processing (without flip-over) using gradient in the image processing method according to an embodiment of the invention.

FIG. 6 is a flow chart of MIP processing (without flip-over) using gradient in the image processing method of the present embodiment. This is a method for calculating each pixel on the screen, and the following calculation is conducted for all the pixels on the image. First, from a projection position, a projection starting point O(x,y,z) and a sampling interval ΔS(x,y,z), a virtual ray direction D(x,y,z) are set (Step S301).

Next, a maximum value M is initialized as a minimum value of the system and a current calculation position X(x,y,z) as "O" (Step S302). Then, from voxel data in the neighbor of a position X(x,y,z), an interpolated voxel value V of the position X is obtained (Step S303).

Next, the value of V is checked (Step S304), and when the value of V is determined as "possibly excluded", the gradient G at the position X is calculated (Step S305). Then, the gradient G is compared with a threshold value T (Step S306), and when f(G,D) is equal to or smaller than the threshold value T (no), M and V are compared (Step S307). When M<V is true (yes), V is assigned to M as a new Maximum value (Step S308).

Next, it is determined whether X reaches a final position or not (Step S309). When X is not at the final position (no), Δ(x,y,z) is added to X(x,y,z), the current calculation position is moved on (Step S310), and the processes of and after Step S303 are repeated. On the other hand, when X reaches the final position (yes), the maximum value M is used as a pixel value of the pixel under calculation (Step 311).

Second Embodiment (MIP Processing—Gradient is Used with Flip-Over)

Figure 7A:
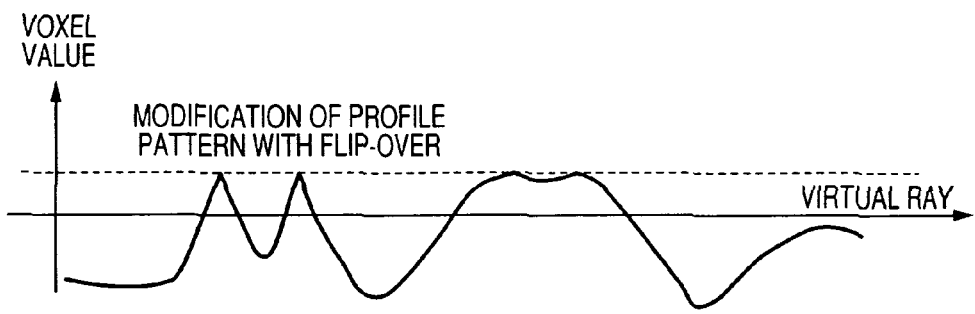
FIGS. 7A, 7B and 7C are drawings for explaining characteristics of voxel values profile along a virtual ray, showing the case when gradient and flip-over are used for the MIP processing in the image processing method according to a second embodiment of the invention.
Figure 7B:
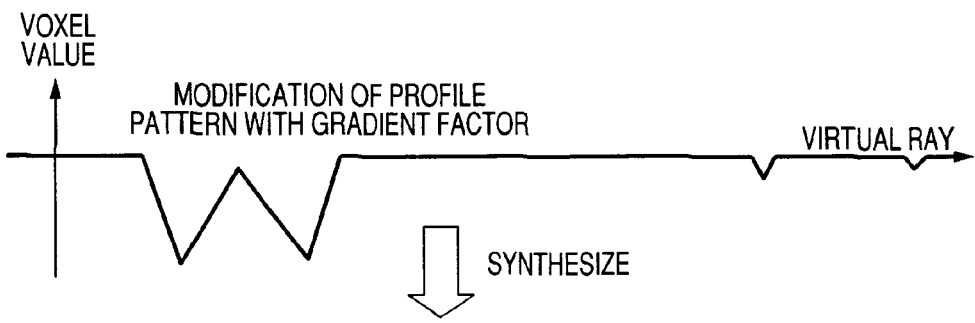
Figure 7C:
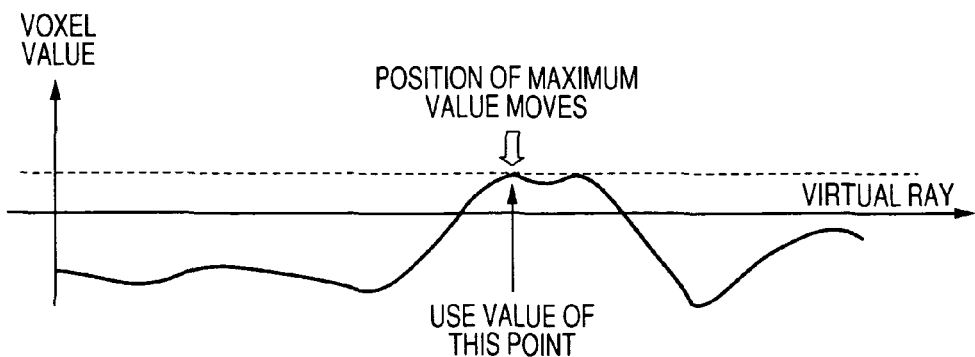

FIGS. 7A, 7B and 7C are explanatory drawings of the case when gradient and flip-over are used for the MIP processing in the image processing method of the present embodiment. In the image processing method of the present embodiment, a first profile pattern is modified using "flip-over" and "gradient factor". Thereby, the position of the maximum value changes, and hence the changed maximum value is utilized. That is, a second profile pattern can be generated by replacing the data on the first profile pattern. By conducting such processing, as compared with the case when the exclusion is performed just by determining a range with thresholds for removing an obstacle on the virtual ray, smoother change can be applied to the image. Thus, in rendering, it can be prevented that the boundary of the excluded region appears as alias. Furthermore, more flexibility can be enhanced in the image processing.

In the present embodiment, the first profile pattern is processed to generate the second profile pattern, and a maximum value is obtained on the second profile pattern. In the MIP processing of the related art, the maximum value is obtained on the first profile pattern. However, since the maximum value does not necessarily correspond to the portion to be observed, sometimes the calcified region is displayed on the screen as a result. On the other hand, when the replacement is conducted, as the position of the maximum value moves on the profile pattern, a more suitable value may be employed as the maximum value.

Figure 8A:
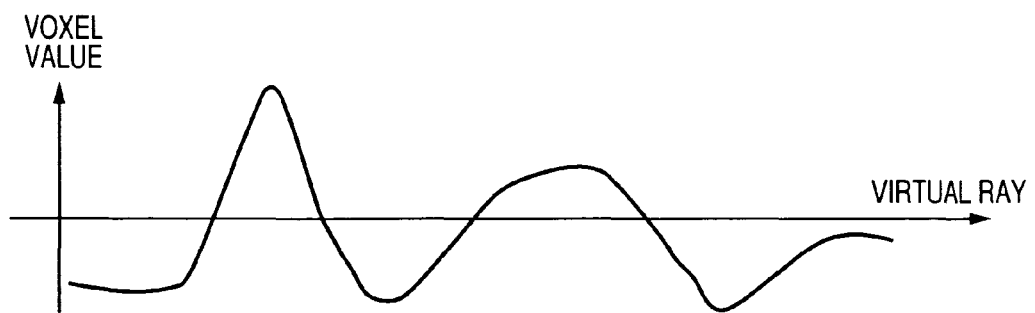
FIGS. 8A, 8B and 8C are drawings for explaining characteristics of voxel values profile along a virtual ray, showing modification of a profile pattern with a gradient factor.
Figure 8B:
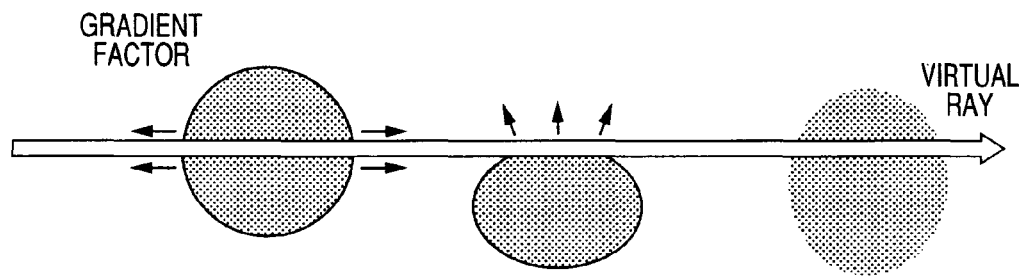
Figure 8C:
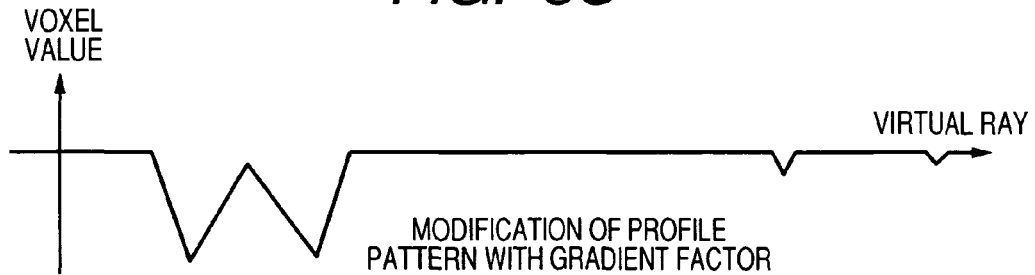
Figure 9A:
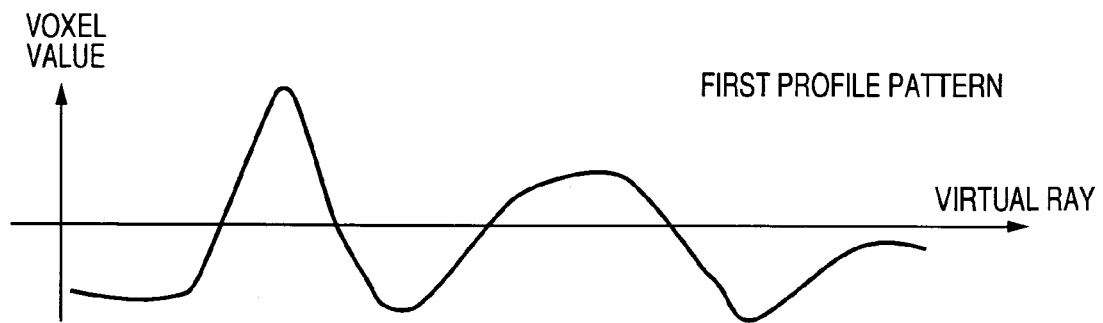
FIGS. 9A and 9B are drawings for explaining characteristics of voxel values profile along a virtual ray, showing modification of a profile pattern with flip-over.
Figure 9B:
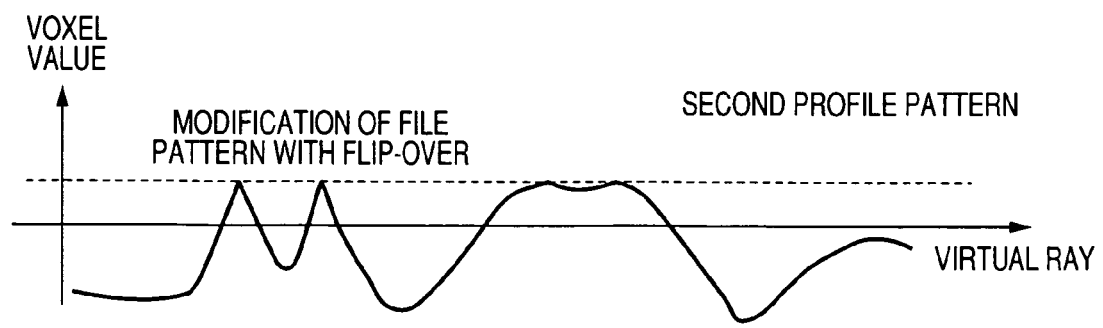

FIGS. 8A, 8B and 8C are explanatory drawings showing modification of a profile pattern with a gradient factor. Moreover, FIGS. 9A and 9B are explanatory drawings showing modification of a profile pattern with flip-over. The transformation of the profile pattern equals to transforming each point on the profile pattern by a function. That is, assuming that the voxel value is V, a flipped-over voxel value is flipV, the virtual ray vector is R, the gradient G=grad(V), the magnitude of the gradient L=|G|, and the angle with the virtual ray θ=arccos (G·R/(|G|·|R|)), a voxel value V2 of the transformed profile pattern is calculated as V2=f(flipV, L, θ). In this case, f may be any function. Here, f(flipV, L, θ)=flipV*LUT(L, θ):lookup table is exemplified.

Figure 10:
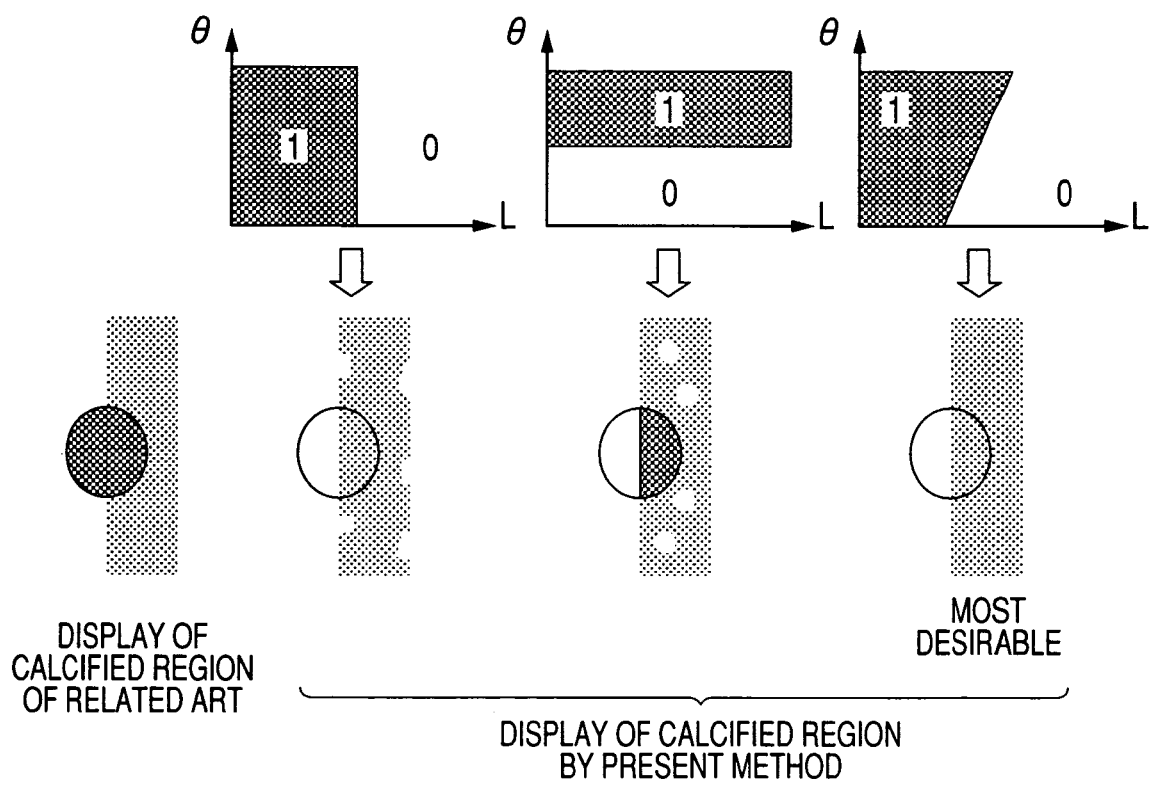
FIG. 10 is an explanatory drawing of examples of LUT function and a display of a calcified region.

FIG. 10 is an explanatory drawing of examples of LUT function and a display of a calcified region. In the usual display of a calcified region, the outline is unclear. However, in the display of a calcified region by the present method, the outline is clear. Also, more desirable image is obtained by considering both the direction and magnitude of the gradient as shown in FIG. 10. Furthermore, the LUT function is exemplified with a binary function for explanation, but the LUT function may be a multi-valued function. Thereby, a smoother result image is obtained.

Figure 11:
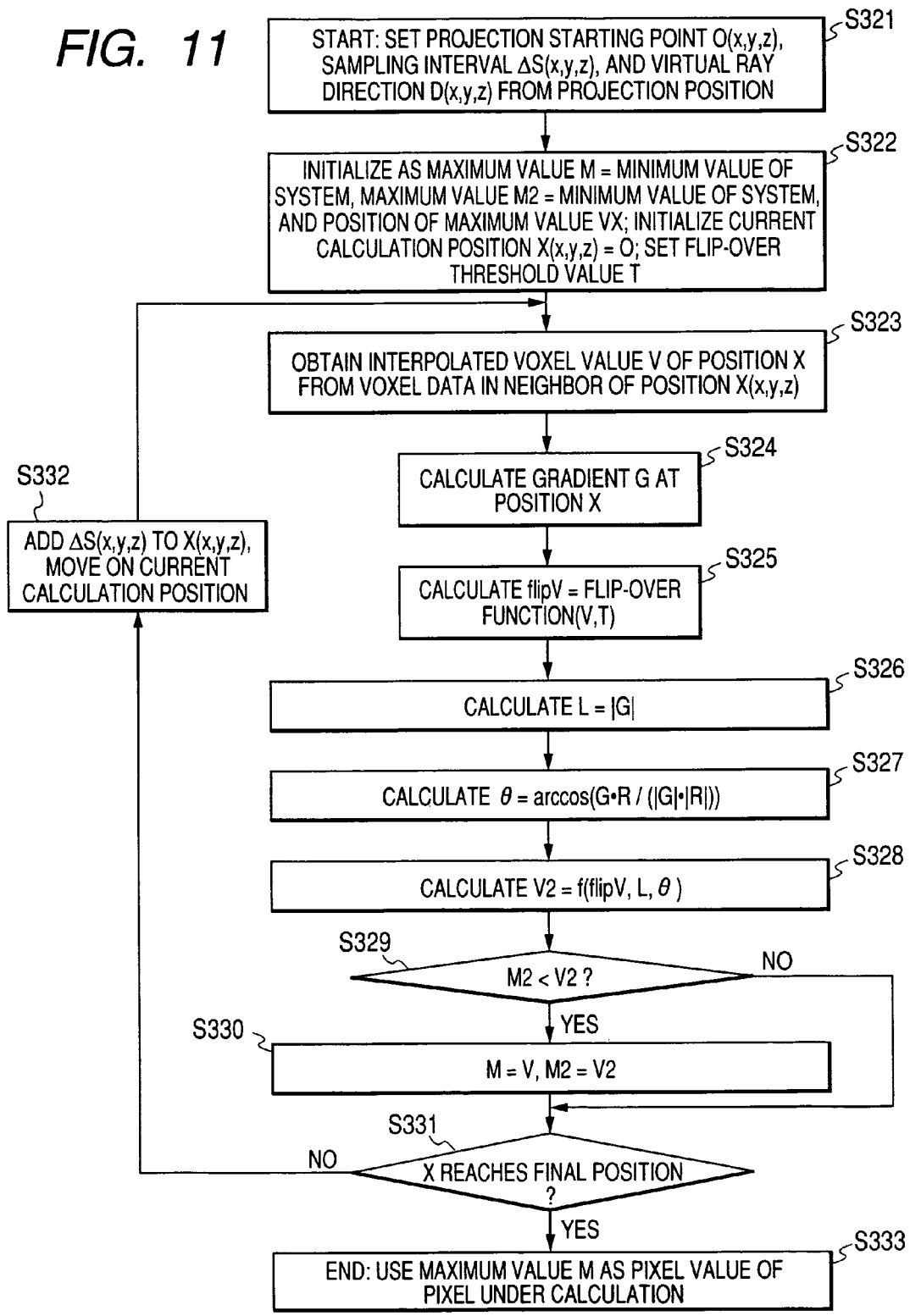
FIG. 11 shows a flow chart of MIP processing using gradient and flip-over in the image processing method according to a second embodiment of the invention.

FIG. 11 shows a flow chart of MIP processing using gradient and flip-over in the image processing method of the present embodiment. This is a method for calculating each pixel on the screen, and the following calculation is conducted for all the pixels on the image. First, from a projection position, a projection starting point O(x,y,z), a sampling interval ΔS(x,y,z) and a virtual ray direction D(x,y,z) are set (Step S321).

Next, a maximum value M is initialized as a minimum value of the system, a maximum value M2 as the minimum value of the system, a position of the maximum value VX is initialized, a current calculation position X(x,y,z) is initialized as "O", and a flip-over threshold T is set (Step S322). Then, from voxel data in the neighbor of the position X(x,y,z), an interpolated voxel value V of the position X is obtained (Step S323).

Next, the gradient G of the position X is calculated (Step S324), flipV=flip-over function(V,T) is calculated (Step S325), and L=|G| is calculated (Step S326). Then, θ=arccos (G·R/(|G|·|R|)) is calculated (Step S327), and V2=f(flipV, L, θ) is calculated (Step S328). Here, the profile pattern may be dynamically calculated, not being prepared beforehand.

Next, M2 and V2 are compared (Step S329) and when M2<V2 is true (yes), V is assigned to M as a new Maximum value and V2 is assigned to M2 as a new Maximum value (Step S330). Then, whether X reaches a final position or not is determined (Step S331). When X is not at the final position (no), ΔS(x,y,z) is added to X(x,y,z), the current calculation position is moved on (Step S332), and the processes of and after Step S323 are repeated. On the other hand, when X reaches the final position (yes), the maximum value M is used as a pixel value of the pixel under calculation (Step 333).

Third Embodiment (MIP Processing—with Flip-Over)

Figure 12:
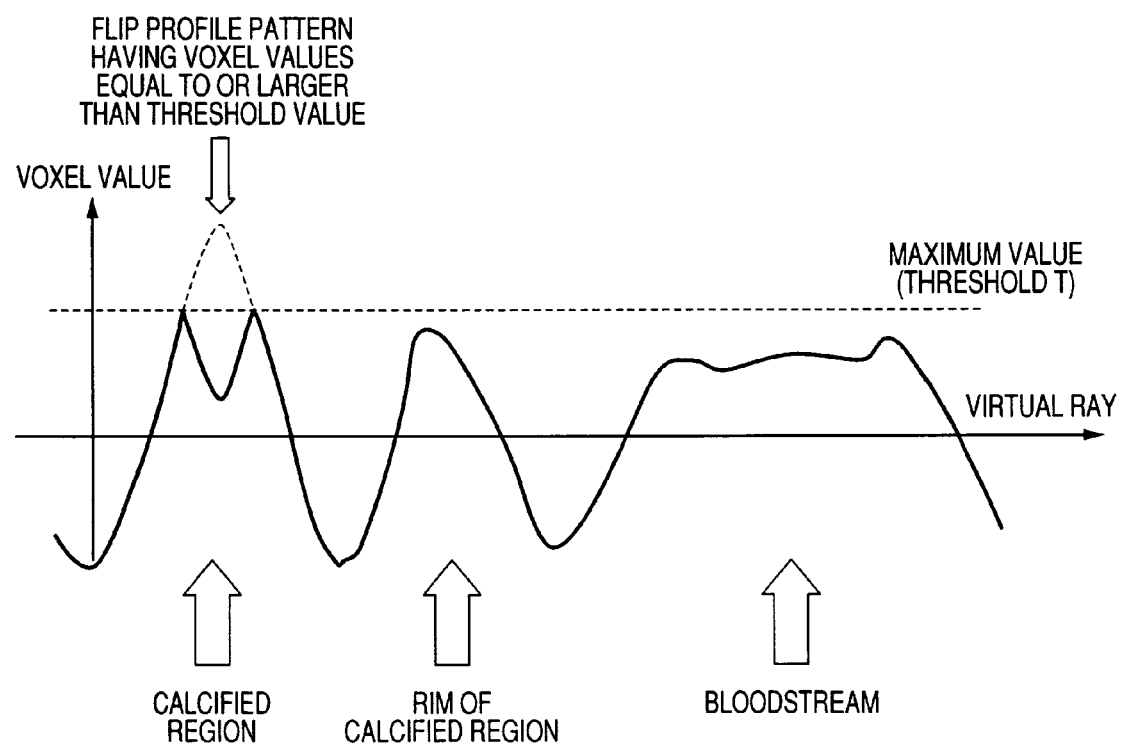
FIG. 12 is a drawing for explaining characteristics of voxel values profile along a virtual ray, showing a procedure 1 wherein the center part of a calcified region is removed, and the bloodstream in front of and at the back of the center part of the calcified region is displayed as well as the rim of the calcified region, in the image processing method according to a third embodiment of the invention.

In the image processing method of the present embodiment, a processing is performed in which a magnitude of a local slope of the profile pattern is calculated for determining whether the calcified region is to be excluded. Furthermore, in order to elicit the magnitude of the local slope, a second profile pattern is generated. FIG. 12 shows a procedure 1 of the present embodiment, wherein the second profile pattern is obtained by replacing the original profile pattern of the virtual ray having equal to or larger than a threshold value, with flip-over. In procedure 1, for example, the second profile pattern is generated, which is a replacing data, by flipping over the profile pattern having voxel values equal to or larger than a threshold value (threshold value T: to be precisely described in FIG. 22) This procedure prevent rendering of a calcified region having high voxel values, and is conducted for excluding the portion where change in the voxel values is large in the next procedure 2, and further, is for highlighting the outline of a rendering object. As a characteristic of the present processing, it is not required to obtain the boundary of a calcified region strictly. Moreover, being compared with the method using a gradient, since the present processing is completed only with the data on the virtual ray, calculation is simple and is conducted at a high speed.

Thereby, in the image processing method of the present embodiment, the outline can be rendered, and rendering of calcified region having high voxel values can be prevented. Moreover, the maximum value (threshold value T) can be easily set, and rendering can be performed with a high reproducibility. Furthermore, the threshold value T can be dynamically changed though GUI by a user, and the user can change the degree of removal of the calcified region while viewing the displayed image.

FIGS. 13A to 13C show profile patterns (1) obtained by the image processing method of the present embodiment, and FIG. 13D shows an image displayed by the image processing method. The profile pattern represents voxel values (inclusive of interpolated voxel values) on the virtual ray. That is, as shown in FIG. 13A, on the virtual ray passing through a bloodstream 22, voxel values corresponding to the bloodstream 22 appear as the profile pattern. Moreover, as shown in FIG. 13B, on the virtual ray passing through a rim 21 of a calcified region, voxel values corresponding to the rim 21 of the calcified region appear as the profile pattern. Furthermore, as shown in FIG. 13C, on the virtual ray passing through the center part of the calcified region 20, voxel values corresponding to the bloodstream 22 instead of the calcified region 20 appear as the profile pattern.

Therefore, in the displayed image, as shown in FIG. 13D, the bloodstream 22 and the rim (outline) 21 of the calcified region are displayed without displaying the center part of the calcified region 20. Also, in the region of the center part of the calcified region 20, the bloodstream 22 exists at the back of the calcified region 20 can be displayed. Accordingly, the size (outline) of the calcified region 20 and the bloodstream 22 of blood vessel narrowed by the calcified region 20 can be obtained by the user at the same time.

Figure 14A:
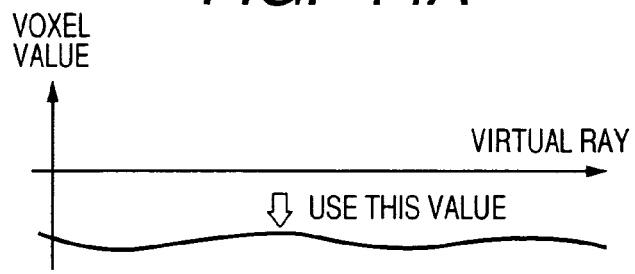
FIGS. 14A to 14C are drawings for explaining characteristics of voxel values profile along a virtual ray, showing profile patterns (2) obtained by the image processing method of according to a third embodiment of the invention.
Figure 14D:
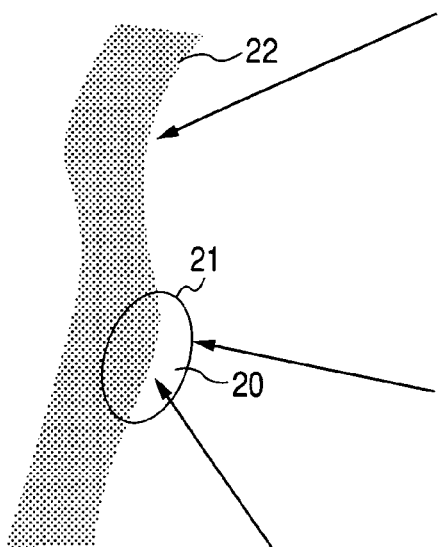
FIG. 14D shows an image displayed by the image processing method according to a third embodiment of the invention.
Figure 14B:
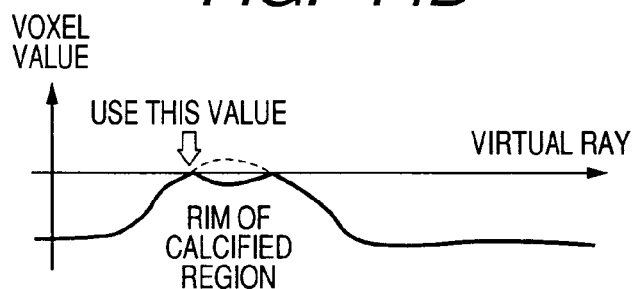
Figure 14C:
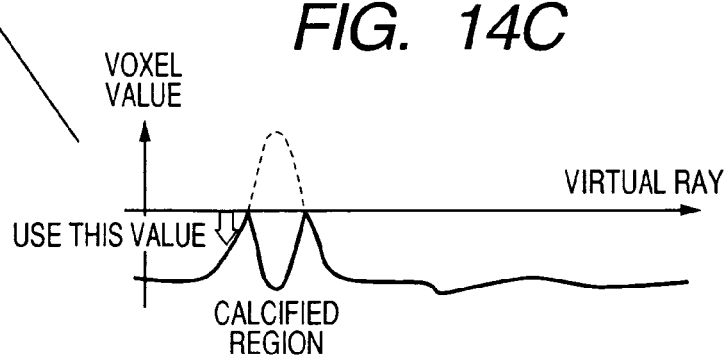

FIGS. 14A to 14C show profile patterns (2) obtained by the image processing method of the present embodiment, and FIG. 14D shows an image displayed by the image processing method. That is, as shown in FIG. 14A, when the bloodstream 22 hardly exists, voxel values as same as those of neighboring tissue are employed. Moreover, as shown in FIG. 14B, for the virtual ray passing through the rim 21 of a calcified region, voxel values corresponding to the rim 21 of the calcified region are employed. Furthermore, as shown in FIG. 14C, for the virtual ray passing through the center part of the calcified region 20, a maximum value other than the excluded range, for example, voxel value corresponding to the neighborhood of the calcified region 20 is employed, since the bloodstream 22 does not exists in front of or at the back of the calcified region 20. Thereby, a user can precisely obtain the size (outline) of the calcified region 20 while viewing the image.

Figure 15:
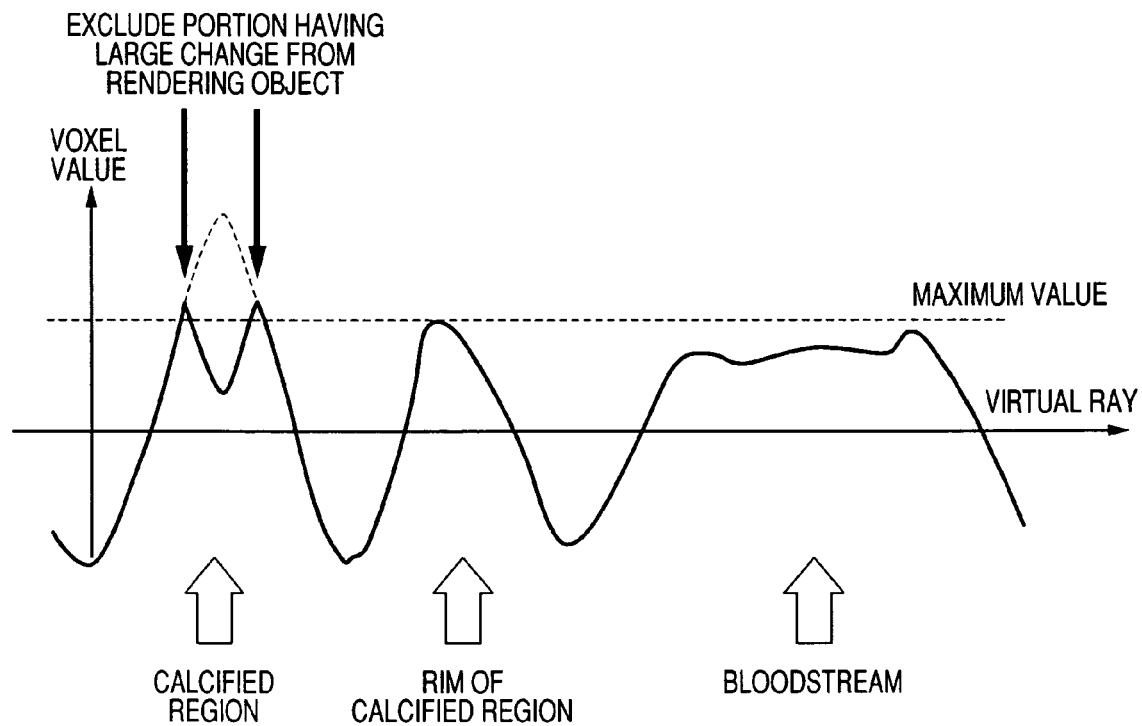
FIG. 15 is a drawing for explaining characteristics of voxel values profile along a virtual ray, showing a procedure 2 in the image processing method according to a third embodiment of the invention.

FIG. 15 shows a procedure 2 in the image processing method of the present embodiment. In the procedure 2, in order to exclude the portion having a large change from the rendering object, for example, a portion on the virtual ray where the absolute value of second order derivative is larger than the threshold value is excluded. Thereby, the rim of the calcified region is rendered so as to obtain the size of the calcified region. In addition, the bloodstream in front of and at the back of the calcified region can be rendered, which is difficult to be rendered in the related art. This processing avoids that, after the flip-over processing in procedure 1, the threshold value at which voxel values are flipped-over is necessarily selected as a maximum value on the virtual ray.

Figure 16A:
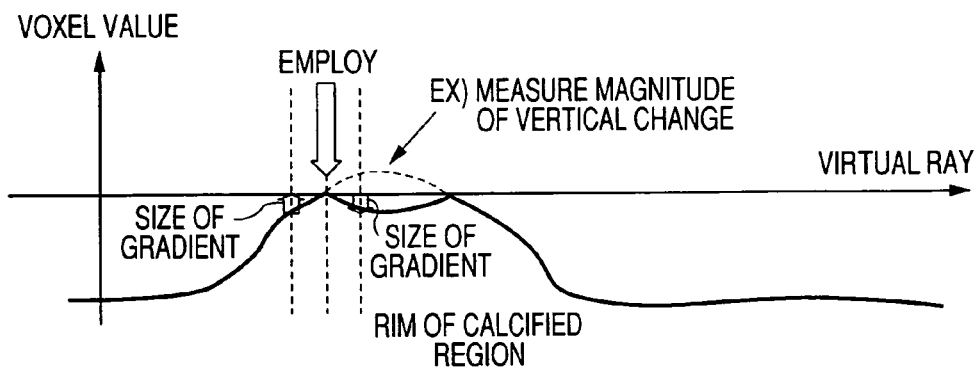
FIGS. 16A and 16B are drawings for explaining characteristics of voxel values profile along a virtual ray, showing a determining method (2) in procedure 2 for determining whether a voxel value corresponding to the virtual ray is to be excluded or not, in the image processing method according to a third embodiment of the invention.
Figure 16B:
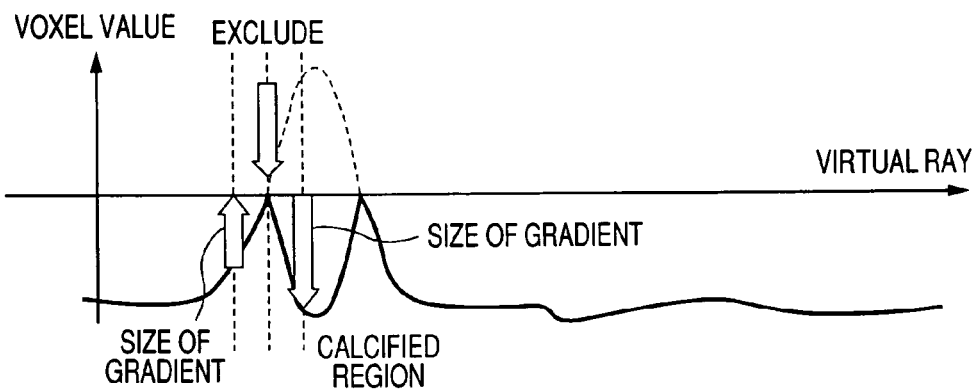

FIGS. 16A and 16B are explanatory drawings of determining method (2) in procedure 2 for determining whether a voxel value corresponding to the virtual ray is to be excluded. FIG. 16A shows a profile of voxel values in the case when the virtual ray passes through the rim of the calcified region. In this case, for example, the magnitude of vertical change (in the direction of the voxel value axis) of the voxel values, or slope of the voxel value profile is measured. Then, for example, the measured magnitude of vertical change in the voxel values, or the measured slope of the voxel value profile is compared with a permissible change threshold value TD (to be precisely described in FIG. 23). Accordingly, it is detected that the region through which the virtual ray passes is the rim of the calcified region, and the voxel is determined as data to be displayed.

On the other hand, FIG. 16B shows a profile pattern in the case when the virtual ray passes through the center part of the calcified region. In this case, for example, the magnitude of vertical change in the voxel values, or the magnitude of gradient of the voxel values is measured. Accordingly, it is detected that the region through which the virtual ray passes is the center part of the calcified region. Then, the voxels in a certain range on the profile pattern are excluded from the data to be displayed. Thereby, only the rim, i.e., the outline of the calcified region can be rendered without rendering the center part of the calcified region. Furthermore, the bloodstream existing in front of and at the back of the center part of the calcified region can be rendered. Moreover, the permissible change threshold value TD can be dynamically changed though GUI by a user, and the user can change the degree of removal of the calcified region while viewing the displayed image.

Figure 17:
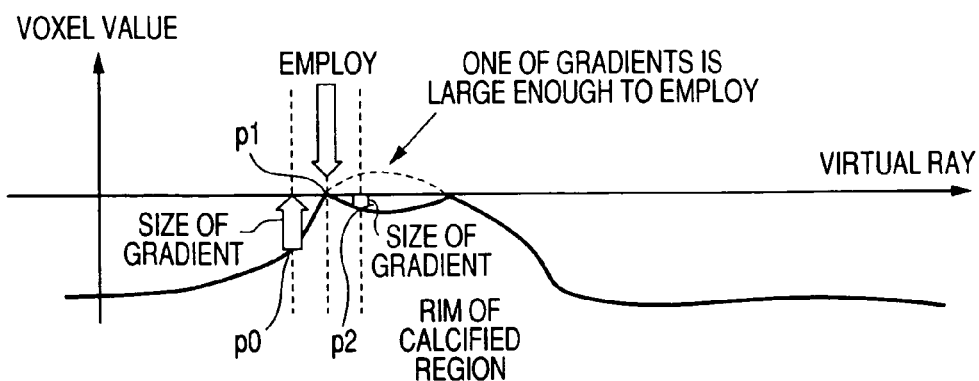
FIG. 17 is a drawing for explaining characteristics of voxel values profile along a virtual ray, showing a determining method (3) in procedure 2 for determining whether a voxel value corresponding to the virtual ray is excluded or not, in the image processing method according to a third embodiment of the invention.

FIG. 17 is an explanatory drawing of determining method (3) in procedure 2 for determining whether a voxel value corresponding to the virtual ray is excluded, and shows a profile of voxel values in the case when the virtual ray passes through the rim of the calcified region. In this case, the magnitude of the gradients before and after a flip-over point (spike) is referred to. Since only one of the gradients before and after the flip-over point is large, this portion is determined as the rim of the calcified region, and is employed as display data. For simplification, second order derivative values may be obtained using the voxel values before and after the flip-over point instead of referring 2 gradients. Conditional expression using Second order derivative may be given by the following.

$$p0-2*p1+p2>\text{threshold}$$

Fourth Embodiment (MIP Processing—with Transformation with Threshold Cutting)

Figure 18A:
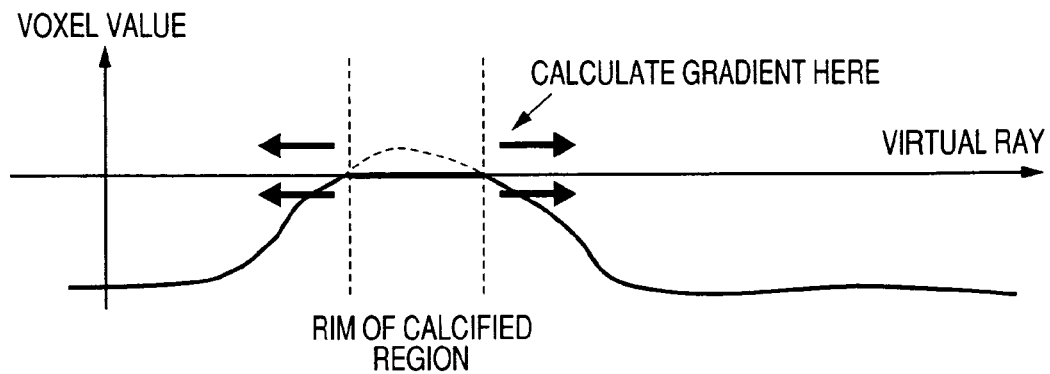
FIGS. 18A and 18B are drawings for explaining characteristics of voxel values profile along a virtual ray, showing the case when the rim of the calcified region is detected employing a transformation method other than the flip-over which uses a threshold value in the image processing method according to a fourth embodiment of the invention.
Figure 18B:
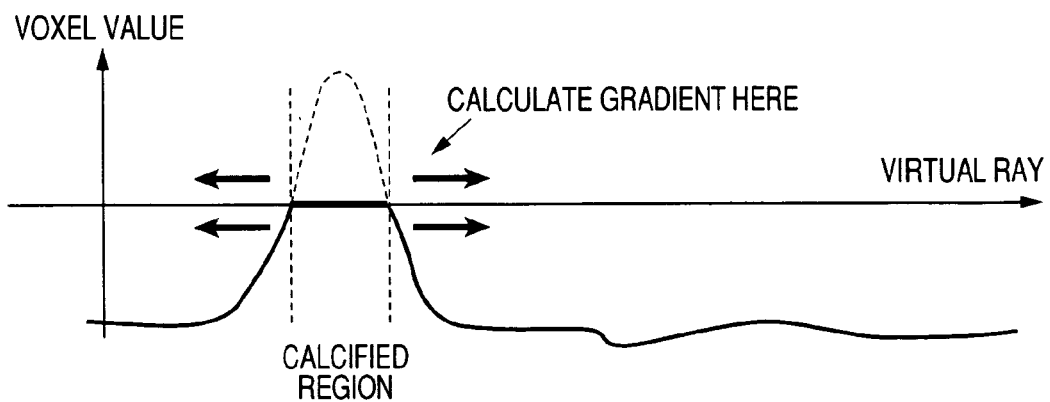

In the second and the third embodiments, flip-over processing is performed on a voxel value profile. Alternatively, other transformation method may be applied to the profile. FIGS. 18A and 18B show explanatory drawings of the case when the rim of the calcified region is detected employing a transformation method other than the flip-over. In this embodiment, the voxel values are not flipped over at a threshold value, but the voxel values are rounded at a threshold value. Then, gradient of the rounded voxel value is calculated, and the voxel is determined to be excluded from or employed in display data by the change in the gradient.

That is, as shown in FIG. 18A, when the gradient of the voxel values rounded at a certain threshold is small, the rounded region is determined as the rim of the calcified region, and is employed as display data. On the other hand, as shown in FIG. 18B, when the gradient of the voxel values rounded at a certain threshold is large, the rounded region is determined as the center part of the calcified region, and is excluded from the display data. According to this method, it is possible to determine whether the voxel is to be excluded from or employed in the display data without the flip-over process at a threshold value.

Fifth Embodiment (MIP Processing—Original Data is Used with Flip-Over)

Figure 19A:
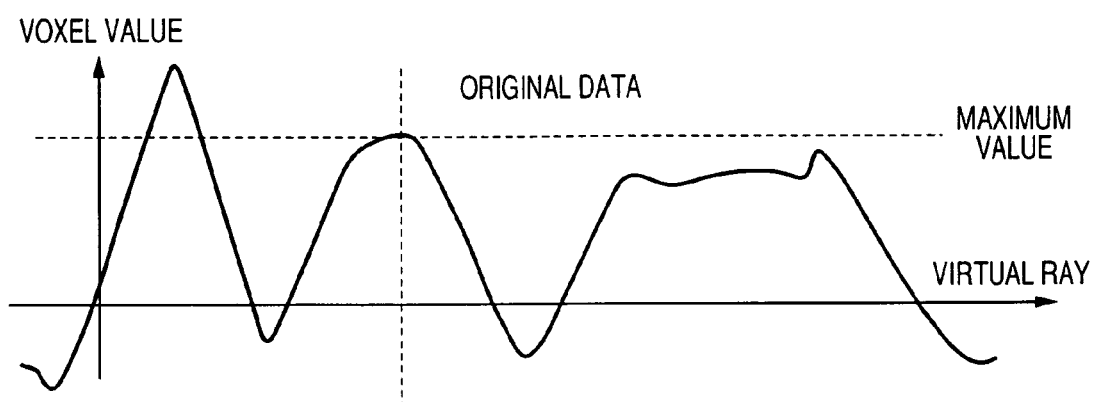
FIGS. 19A and 19B are drawings for explaining characteristics of voxel values profile along a virtual ray, showing a procedure 3 in the case when the original data before flip-over is employed as display data of the rim of the calcified region in the image processing method according to a fifth embodiment of the invention.
Figure 19B:
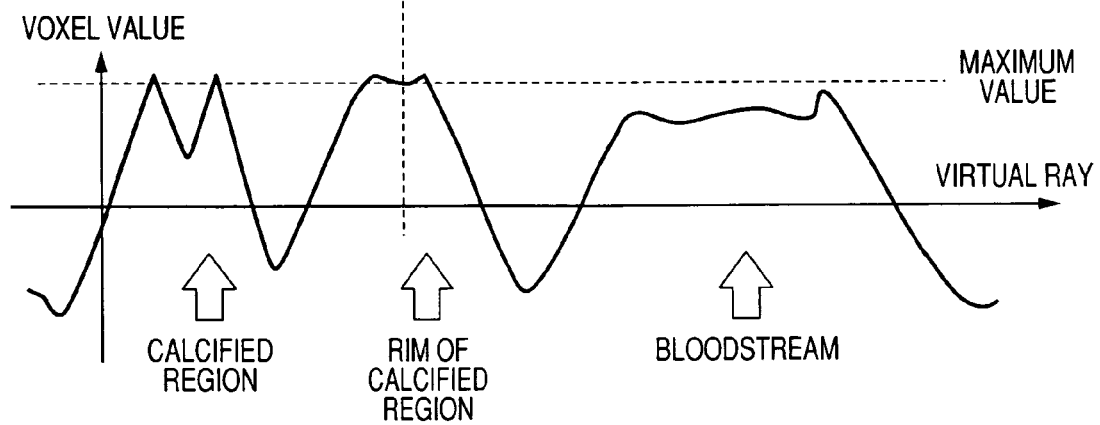

In the second and the third embodiments, flip-over processing is performed on a voxel value profile, and data on the transformed profile is selected as a display data. However, it is preferable that the display data is obtained from the original profile rather than the transformed profile. FIGS. 19A and 19B show a procedure 3 in the case when the original data before flip-over is employed as display data of the rim of the calcified region in the image processing method of the present embodiment. In the present embodiment, the user can dynamically set the threshold of the flip-over processing through GUI to make it close to the maximum value in the region to be displayed. However, depending on the position through which the virtual ray passes, the voxel values corresponding to the rim of the calcified region may become an object to be flipped over as shown in FIG. 19B. In this case, as shown in FIG. 19A, by using the voxel values (original data) corresponding to the rim of the calcified region before the flip-over processing, the rim of the calcified region can be clearly rendered.

Sixth Embodiment (Preferred Embodiment—MIP Processing with Flip-Over)

Figure 20A:
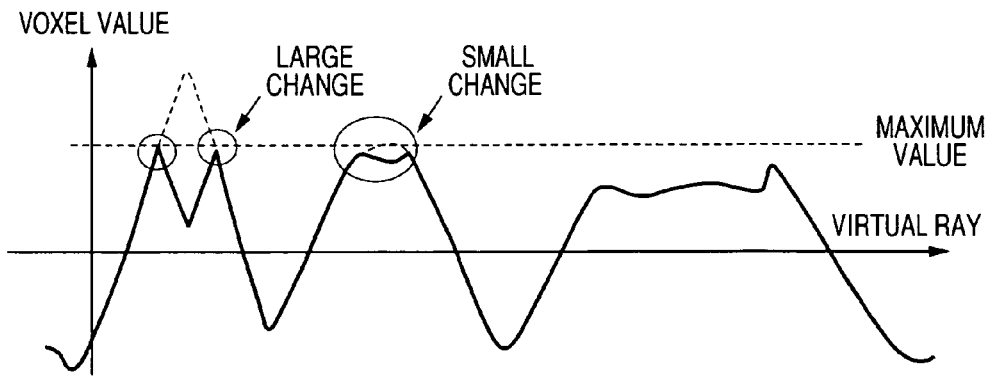
FIGS. 20A and 20B are drawings for explaining characteristics of voxel values profile along a virtual ray, showing preferable examples in the image processing method according to a sixth embodiment of the invention.
Figure 20B:
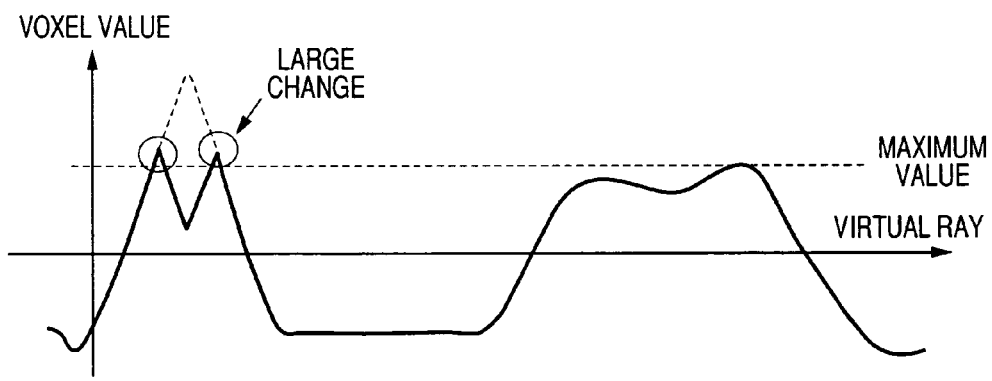

FIGS. 20A and 20B show preferable examples in the image processing method of the present embodiment. FIG. 20A shows a case when the center part of the calcified region, the rim of the calcified region, and the bloodstream exist on the virtual ray. By performing the flip-over processing at a threshold value to detect the magnitude of change in voxel values, it is determined whether the region through which the virtual ray passes is the center part of the calcified region or the rim of the calcified region. Therefore, only the rim of the calcified region can be displayed without displaying the center part of the calcified region.

Moreover, FIG. 20B is a case when the center part of the calcified region and the bloodstream exist on the virtual ray. By performing the flip-over processing at a maximum value to detect the magnitude of change in voxel values, the center part of the calcified region is determined. Therefore, only the bloodstream existing at the back of the center part of the calcified region can be displayed without displaying the center part.

Figure 21A:
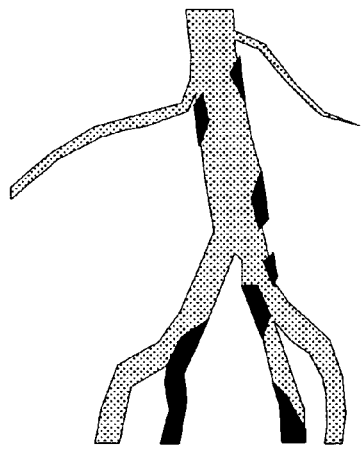
FIG. 21A shows an example of an MIP image of the related art.
Figure 21B:
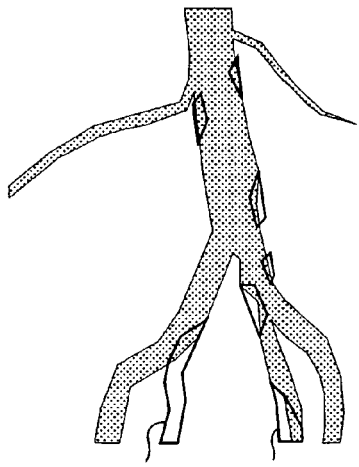
FIG. 21B shows an example of an MIP image generated by the image processing method according to embodiments of the invention.

FIG. 21A shows an example of an MIP image of the related art, and FIG. 21B shows an example of an MIP image generated by the image processing method of the present embodiment. In the MIP image shown in FIG. 21A, the bloodstream in front of and at the back of the calcified region is not clear by the presence of the calcified region. However, the MIP image of the present embodiment shown in FIG. 21B, only the outline of the calcified region is displayed, and the user can obtain whether the bloodstream remains or not in front of and at the back of the calcified region.

Figure 22:
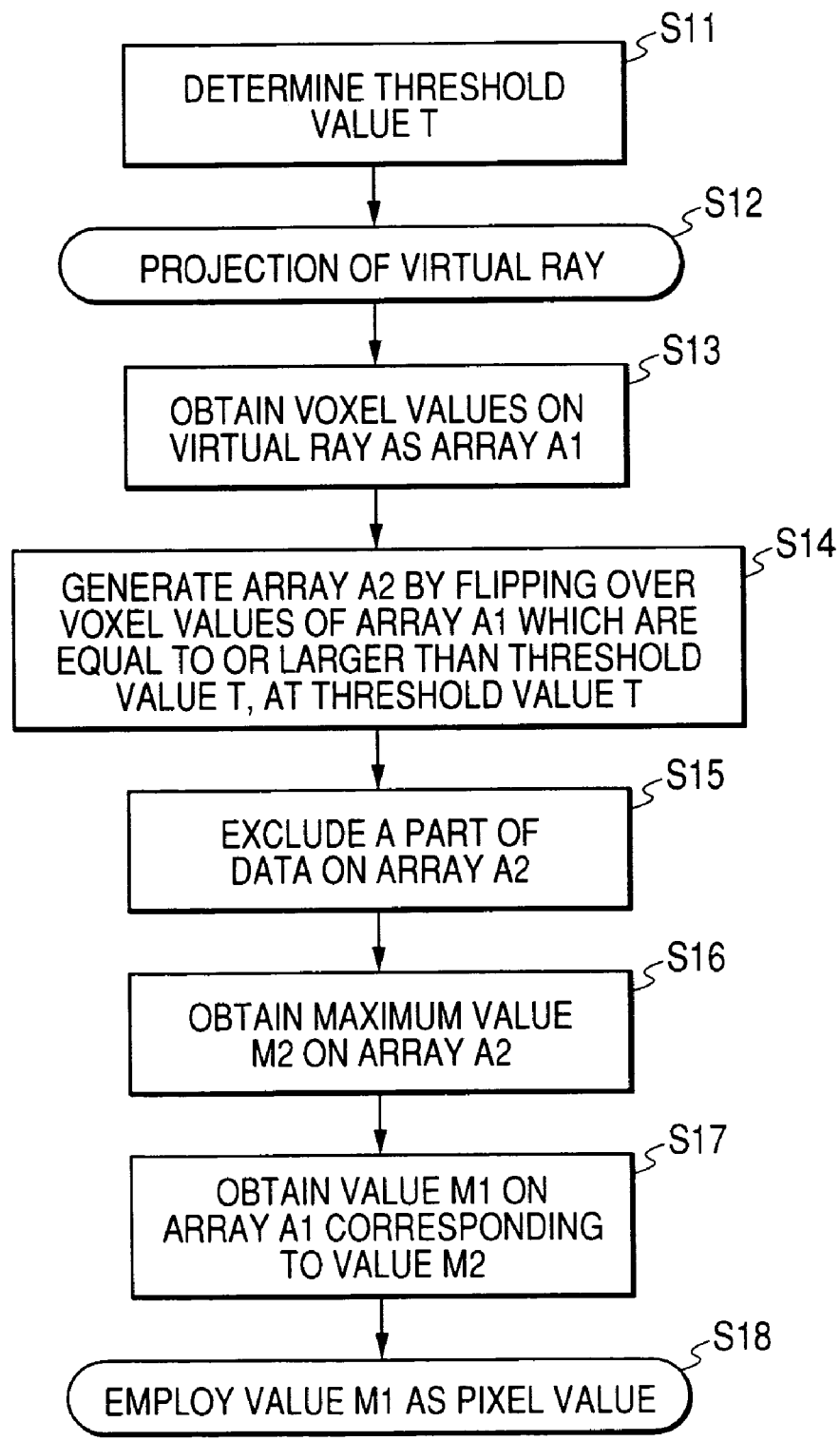
FIG. 22 shows a flow chart illustrating q processing for obtaining each pixel value of an image in the image processing method according to a sixth embodiment of the invention.

FIG. 22 shows a flow chart illustrating an entire picture of the processing for obtaining each pixel value of an image in the image processing method of the present embodiment. In order to obtain each pixel value of an image, at first, as shown in FIG. 12, the threshold value T which is a little larger than the voxel values of a target tissue such as bloodstream is determined (Step S11).

Next, a virtual ray is projected (Step S12), and voxel values on the virtual ray are obtained as an array A1 (original (first) profile pattern) (Step S13). Then, an array A2 (second profile pattern) is generated by the voxel values of the array A1 which are equal to or larger than the threshold value T are flipped-over at the threshold value T (Step S14). Then, a part of the data on the array A2, e.g., flipped-over data corresponding to the center part of the calcified region is excluded (Step S15).

Next, a maximum value M2 on the array A2 is obtained (Step S16), and a value M1 on the array A1 (original data in FIG. 19A) corresponding to the value M2 is obtained (Step S17). Then, the value M1 is employed as a pixel value for the virtual ray (Step S18).

In the embodiment, a buffer is generated to obtain the replaced array A2 in Step S14. In the following Step S15, a part of data on the array A2 is excluded. However, it is also possible that the replaced array A2 is dynamically obtained according to the advance of the virtual ray in response to instructions from a user by GUI, and a part of data is excluded progressively. Thereby, the user can precisely observe an object while changing the target object and the direction to observe the object.

Figure 23:
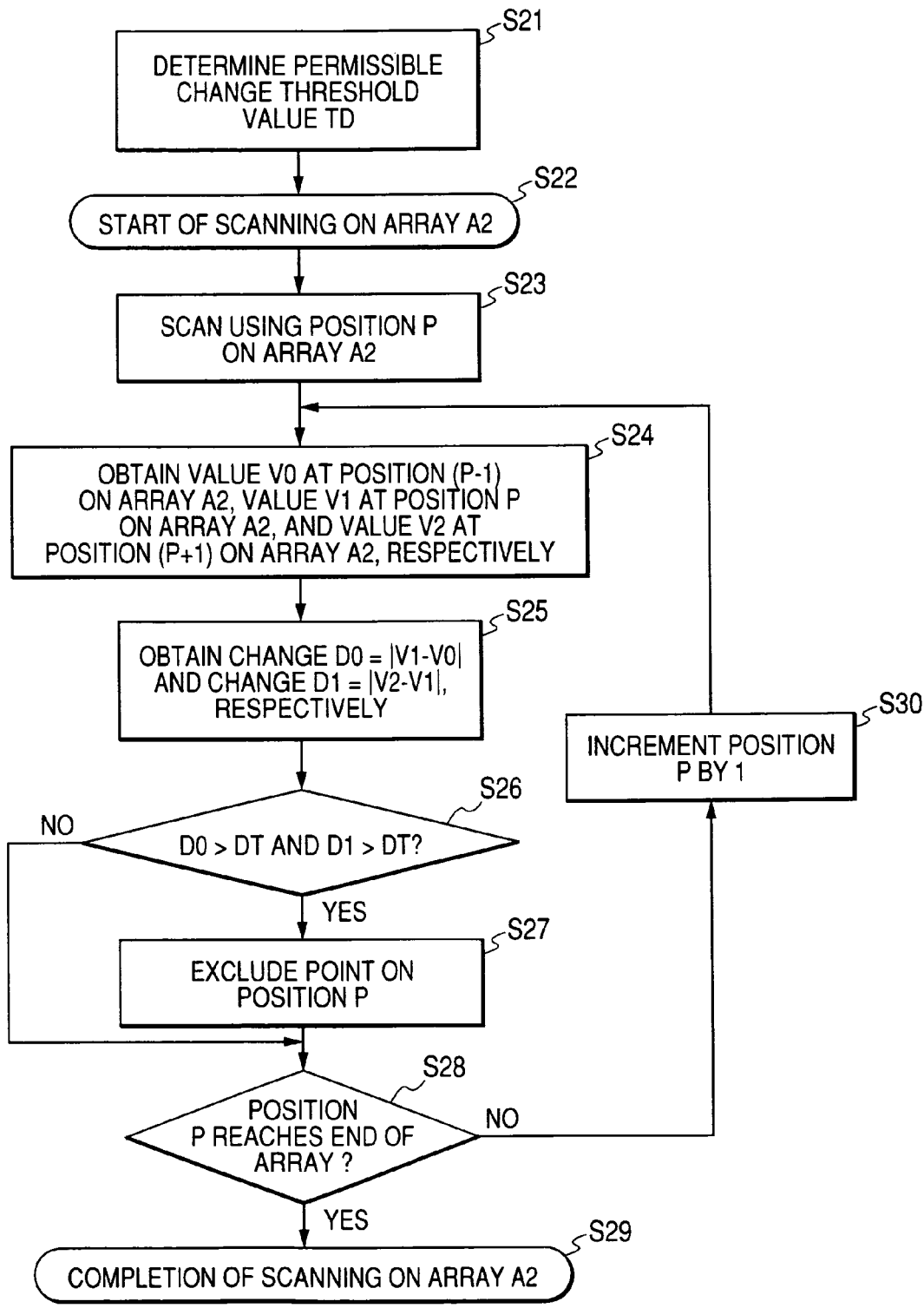
FIG. 23 shows a flow chart of the case when whether data is to be excluded is determined using a change in voxel data in the image processing method according to a sixth embodiment of the invention.

FIG. 23 shows a flow chart of the case when whether data is to be excluded is determined using a change in voxel data in the image processing method of the present embodiment. At first, as shown in FIGS. 16A and 16B, the permissible change threshold value TD is determined for determining the magnitude of change in voxel data (gradient in graph) (Step S21).

Next, scanning on the array A2 is started (Step S22), and scanning is conducted using a position P on the array A2 (Step S23). Then, a value V0 at the position (P−1) on the array A2, a value V1 at the position P on the array A2, and a value V2 at the position (P+1) on the array A2 are respectively obtained (Step S24).

Next, change D0=|V1−V0| and change D1=|V2−V1| are respectively obtained (Step S25), and the change D0 and the change D1 are compared with the permissible change threshold value TD in magnitude (Step S26). Then, when the change D0 and the change D1 are larger than the permissible change threshold value TD (yes), the point on the position P is excluded (Step S27).

On the other hand, when the change D0 and the change D1 are not larger than the permissible change threshold value TD (no), whether the position P reaches the end of the array or not is determined (Step S28). When the position P is not at the end of the array (no), the position P is incremented by 1 (Step S30), and the processing of and after the Step S24 are repeated. On the other hand, in Step S28, when the position P reaches the end of the array (yes), the scanning on the array A2 is completed (Step S29).

Thereby, the center part of the calcified region is not rendered, and only the rim, i.e., the outline is rendered. Furthermore, the bloodstream existing in front of and at the back of the center part of the calcified region can be rendered. Moreover, the permissible change threshold value TD can be dynamically changed though GUI by a user, and the user can change the degree of removal of the calcified region while viewing the displayed image.

Figure 24:
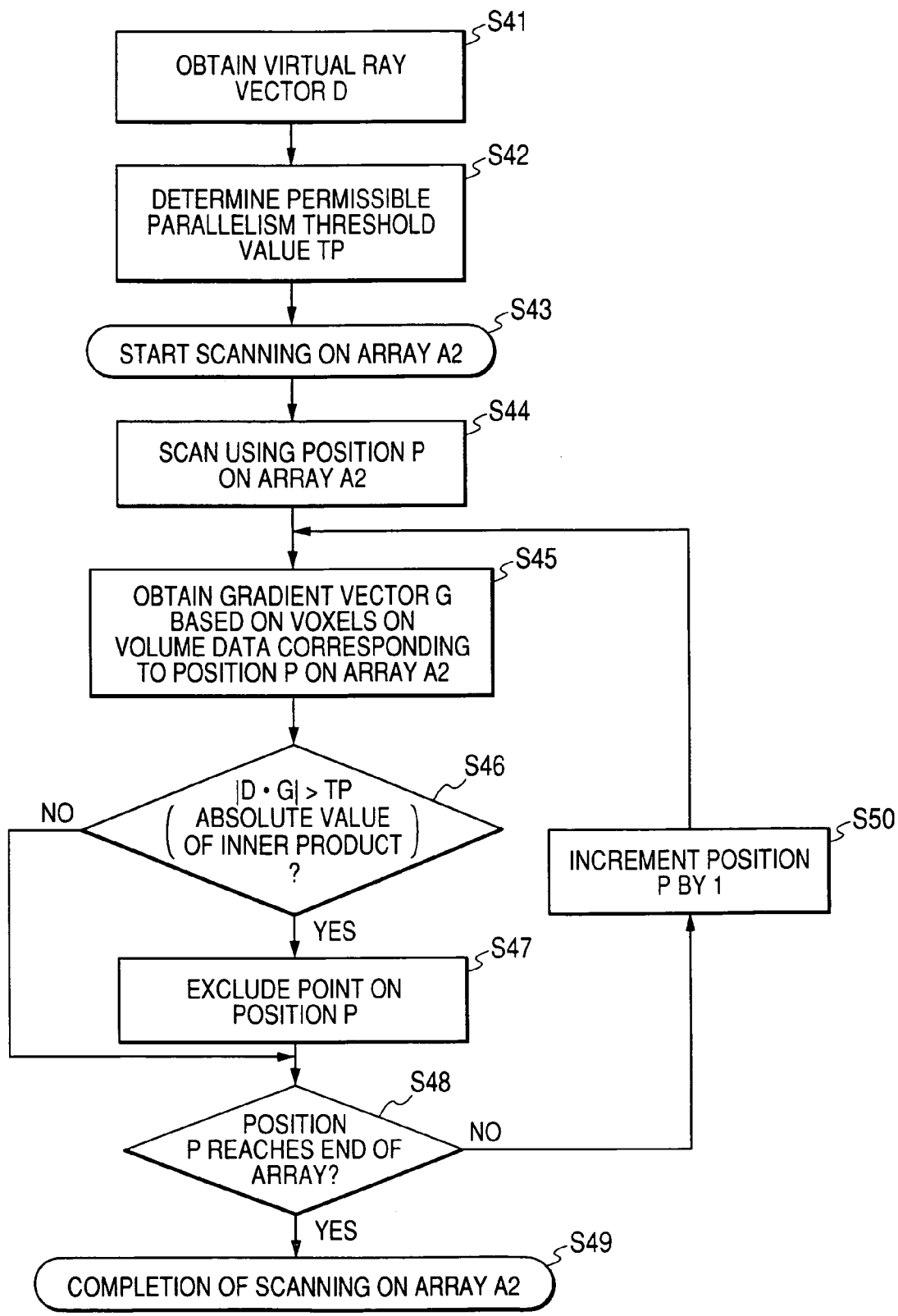
FIG. 24 shows a flow chart of the case when exclusion of data is determined using gradient in the image processing method according to a sixth embodiment of the invention.

FIG. 24 shows a flow chart of the case when exclusion of data is determined using gradient in the image processing method of the present embodiment. In this case, as shown in FIGS. 4A and 4B, at first, the virtual ray vector D is obtained (Step S41), and a permissible parallelism threshold value TP is determined (Step S42).

Next, scanning is started on the array A2 (Step S43), and the scanning is conducted using the position P on the array A2 (Step S44). Moreover, a gradient vector G is obtained based on voxels on the volume data corresponding to the position P on the array A2 (Step S45).

Next, the absolute value of an inner product of the virtual ray vector D and the gradient vector G of the volume data is compared with the permissible parallelism threshold value TP (Step S46). When the absolute value of the inner product of the virtual ray vector D and the gradient vector G is larger than the permissible parallelism threshold value TP (yes), the point on the position P is excluded (Step S47).

On the other hand, when the absolute value of the inner product of the virtual ray vector D and the gradient vector G is not larger than the permissible parallelism threshold value TP (no), whether the position P reaches the end of the array or not is determined (Step S48). When the position P is not at the end of array (no), the position P is incremented by +1 (Step S50), and the processes of and after Step 45 are repeated. On the other hand, when the position P reaches the end of the array (yes), the scanning on the array A2 is completed (Step S49).

Thereby, the portion where the gradient vector G is substantially parallel to the virtual ray vector D of the virtual ray is determined to be the center part of the calcified region, and thus that portion is excluded from display data. On the other hand, the portion where the gradient vector G is substantially perpendicular to the virtual ray vector D is determined to be the rim of the calcified region, and thus that portion is employed as display data. Moreover, the permissible parallelism threshold value TP can be dynamically changed though GUI by a user. The user can change the degree of removal of the calcified region while viewing the displayed image.

Seventh Embodiment (Ray Casting Method—Gradient is Used)

Incidentally, in ray casting method, opacity can be set for each voxel. Thus, opacity can be assigned to the data on the virtual ray without excluding some range on the virtual ray from display data.

According to the above, for example, it becomes possible to display a portion having a sharp gradient of voxel values as a hard portion, and a portion having a gradual gradient of voxel values as a soft portion, and the like. Moreover, thereby, it becomes possible to select and not display the portion having a sharp gradient. Furthermore, since it becomes possible to detect the portion having a sharp gradient (boundary surface of calcification), an image in which the calcified portion is removed can be displayed without masking process.

Figure 25:
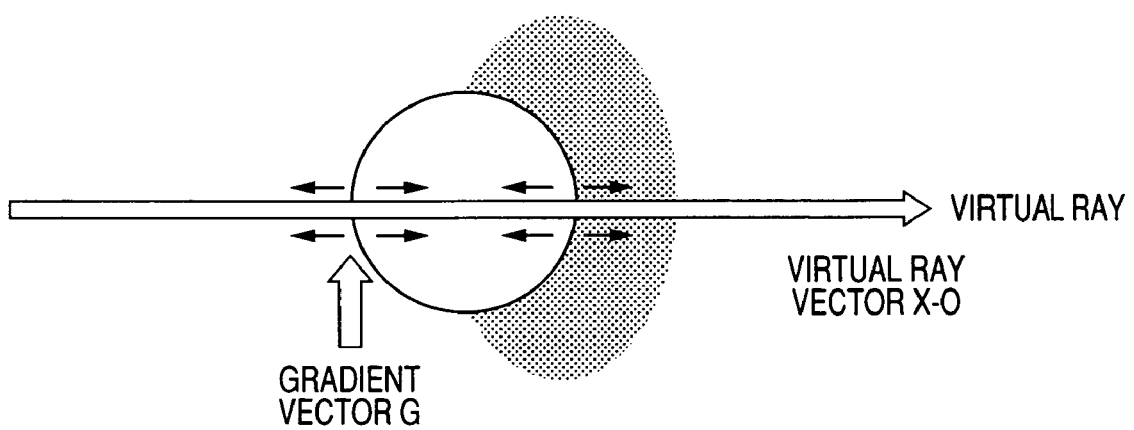
FIG. 25 is an explanatory drawing of the case when the opacity is changed (Application 1 for ray casting method) in the image processing method according to an seventh embodiment of the invention.

FIG. 25 shows an explanatory drawing of the case when an opacity of the obstructing region is changed and the center part of the obstructing region is not displayed (Application 1 for ray casting method). Also by changing the opacity of voxel values of the rendering object, a region to be an obstruction can be excluded. That is, an exclusion degree $\alpha$ of the rendering object is calculated, and the exclusion degree $\alpha$ is associated with the opacity.

In this case, inner product of a virtual ray vector X–O of the flipped-over data and the gradient vector G is used for calculating the exclusion degree $\alpha = |G^*(X-O)|$. Since a portion where the virtual ray vector X–O and the gradient vector G is parallel and the exclusion degree $\alpha$ is high is the central part of the calcified region, the opacity of the voxel values are made low so as not to display the calcified region. Thereby, without performing processes such as calculation for flip-over, it is possible to display the rim of the calcified region and the bloodstream in front of and at the back of the calcified region, and not display the center part of the calcified region.

Figure 26:
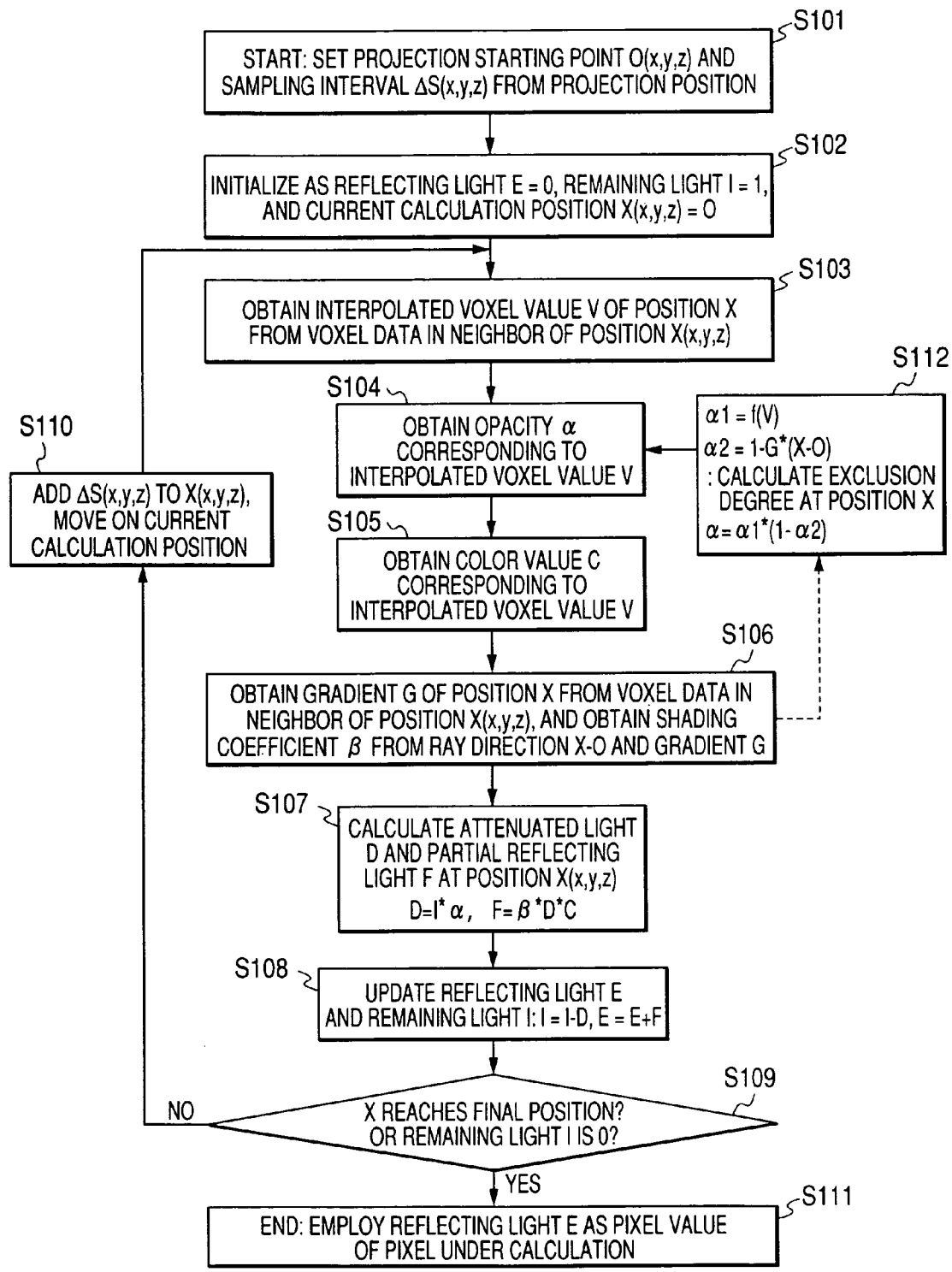
FIG. 26 shows a flow chart of the case when the opacity is changed using gradient (Application 1 for ray casting method) in the image processing method according to an seventh embodiment of the invention.

FIG. 26 shows a flow chart of the case when the opacity is changed using gradient of voxel values (Application 1 for ray casting method). This processing is a calculation for each pixel on the screen, and the following calculation is conducted for all the pixels on the image. First, from a projection position, a projection starting point O(x,y,z) and a sampling interval $\Delta S(x,y,z)$ are set (Step S101).

Next, a reflecting light E is initialized as "0", a remaining light I as "1", and a current calculation position X(x,y,z) as "O" (Step S102). Then, from voxel data in the neighbor of the current calculation position X(x,y,z), an interpolated voxel value V of the current calculation position X is obtained (Step S103). In addition, an opacity $\alpha$ corresponding to the interpolated voxel value V is obtained (Step S104). In this case, by $\alpha 1 = f(V)$, $\alpha 2 = 1 - G^*(X-O)$, $\alpha = \alpha 1^*(1-\alpha 2)$, the exclusion degree at the position X is calculated (Step S112).

Next, a color value C corresponding to the interpolated voxel value V is obtained (Step S105). Then, from voxel data in the neighbor of the position X(x,y,z), a gradient G of the position X is obtained. From a ray direction X–O and the gradient G, a shading coefficient $\beta$ is determined (Step S106).

Next, an attenuated light D (D=I*$\alpha$) and a partial reflecting light F (F=$\beta$*D*C) at the position X(x,y,z) are calculated (Step S107). Then, the reflecting light E and the remaining light I are updated (I=I−D, E=E+F) (Step S108).

Next, whether the current calculation position X reaches a final position or not, and whether the remaining light I is "0" or not are determined (Step S109). When the current calculation position X is not at the final position and the remaining light I is not "0" (no), $\Delta S(x,y,z)$ is added to X(x,y,z), the current calculation position is moved on (Step S110), and the processes of and after Step S103 are repeated.

On the other hand, when the current calculation position X reaches the final position, or the remaining light I becomes "0" (yes), the calculation is completed by employing the reflecting light E as a pixel value of the pixel under calculation (Step 111). In ray casting method of the related art, a shading coefficient obtained from a product of a gradient of voxel and a light source direction is used for calculating a reflecting light amount. However, as described above, in the present invention, it is possible to detect a calcified region and a two-dimensional boundary surface thereof from a product of the gradient and the virtual ray direction, apart from the physical meaning of gradient. Furthermore, by changing the opacity of voxels according to the detected information, it is possible to display the rim of the calcified region and the bloodstream in front of and at the back of the calcified region without displaying the center part of the calcified region.

Eighth Embodiment (Ray Casting Method—with Flip-Over)

Figure 27:
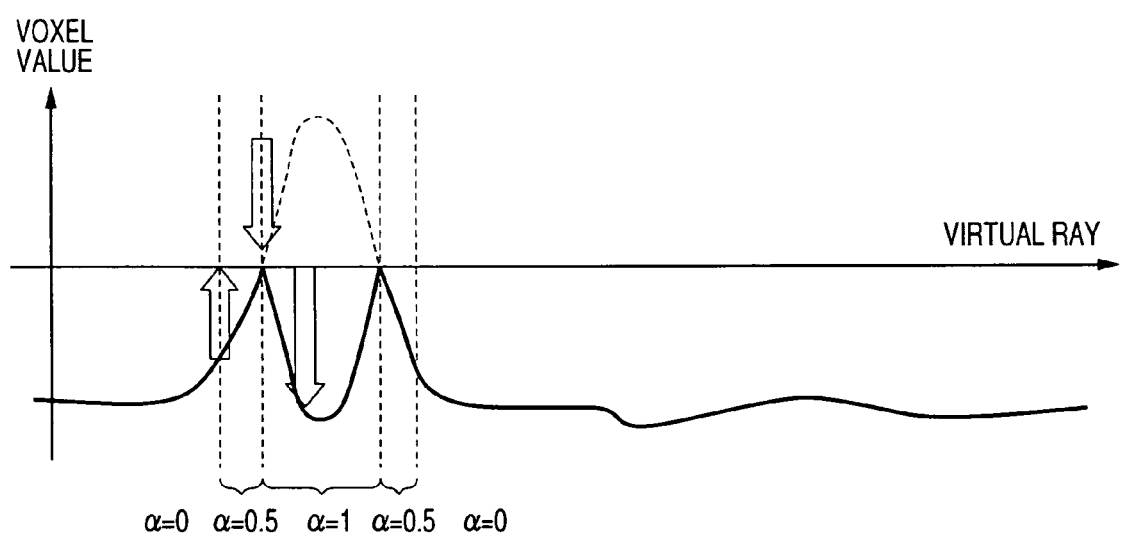
FIG. 27 is a drawing for explaining characteristics of voxel values profile along a virtual ray, showing the case when the opacity is changed (Application 2 for ray casting method) in the image processing method according to a eighth embodiment of the invention.

FIG. 27 shows an explanatory drawing of the case when the opacity is changed (Application 2 for ray casting method). In this case, the exclusion degree α is obtained from the change in the flipped-over voxel values. That is, in the portion to be determined for exclusion, as for flipped-over data, a portion where voxel values are remarkably changed and flipped-over is represented as α=1, a portion where voxel values are remarkably changed but not flipped-over is represented as α=0.5, and the other portion is represented as α=0, for example. Then, the region where α=1 is not displayed, being determined as an obstructing region. The region where α=0.5 is displayed as the rim of the obstructing region. Thus, by obtaining the exclusion degree α from the change in the flipped-over voxel values, it is possible to display the rim of the calcified region and the bloodstream in front of and at the back of the calcified region without displaying the center part of the calcified region.

Figure 28:
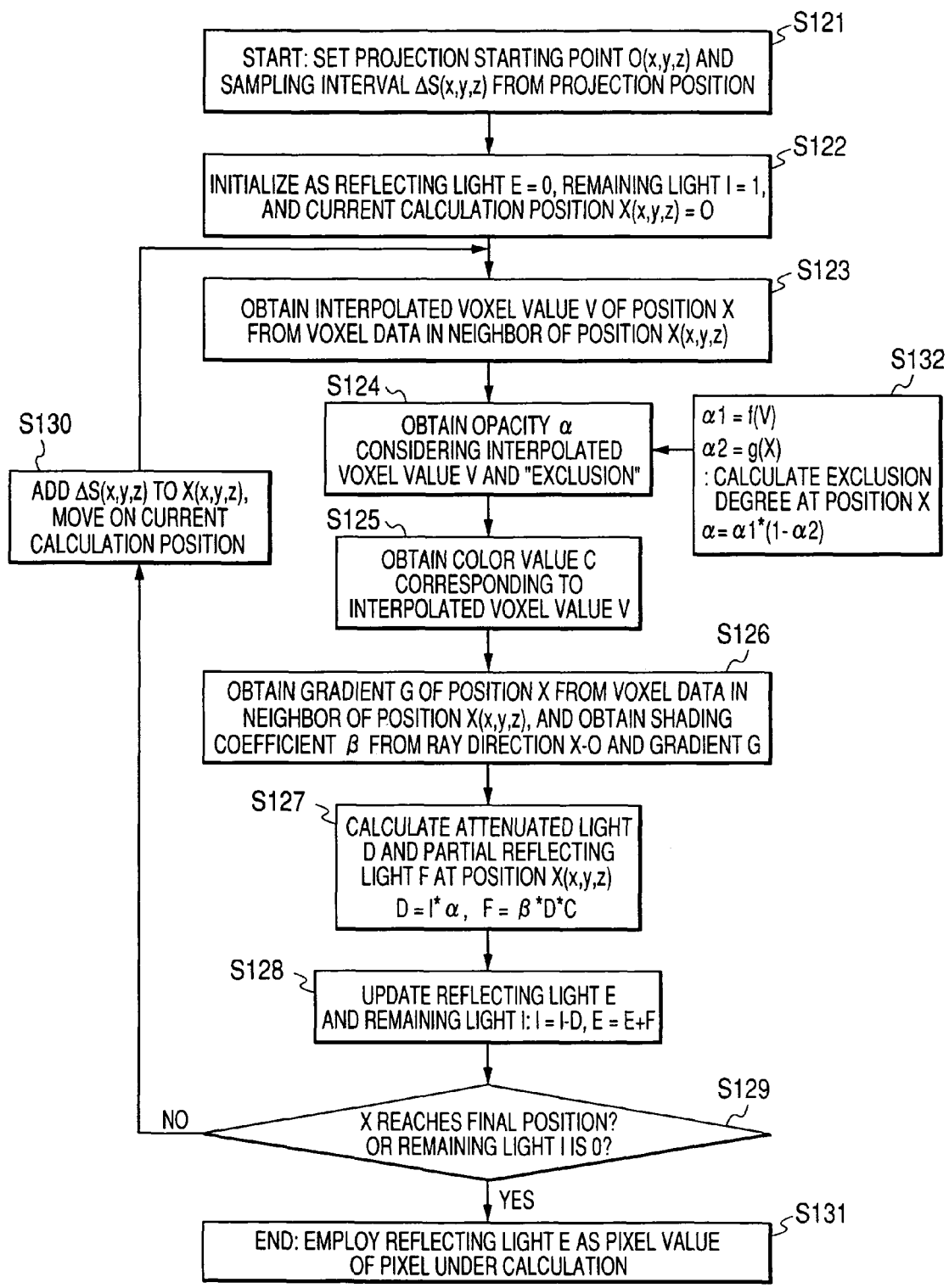
FIG. 28 shows a flow chart of the case when the opacity is changed using the change in voxel values (Application 2 for ray casting method) in the image processing method according to a eighth embodiment of the invention.
Figures 31A, 31B, 31C, 31D:
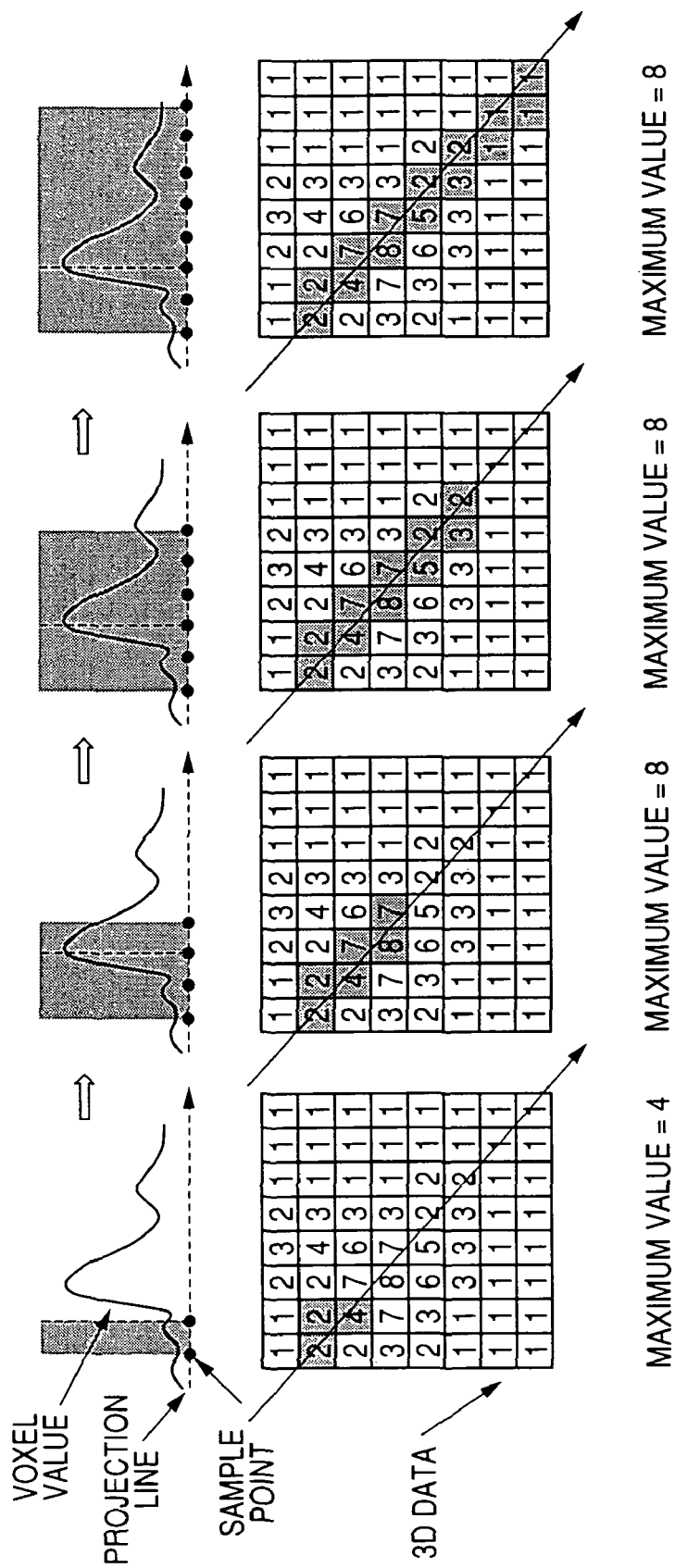
FIGS. 31A, 31B, 31C and 31D are explanatory drawings of MIP processing on voxel values and 3D data.
Figure 32A:
FIG. 32A is an example of a Raycast image.
Figure 32B:
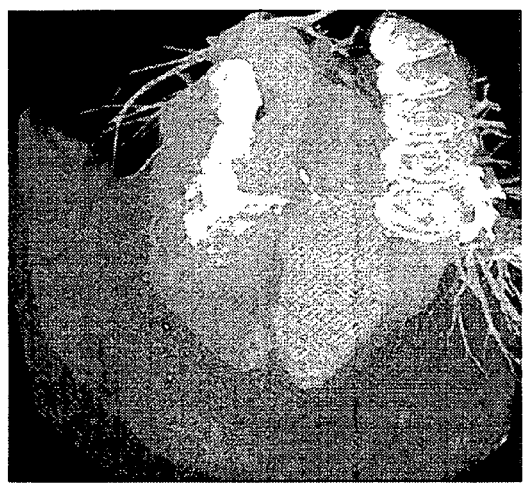
FIG. 32B is an example of an MIP image.
Figure 33A:
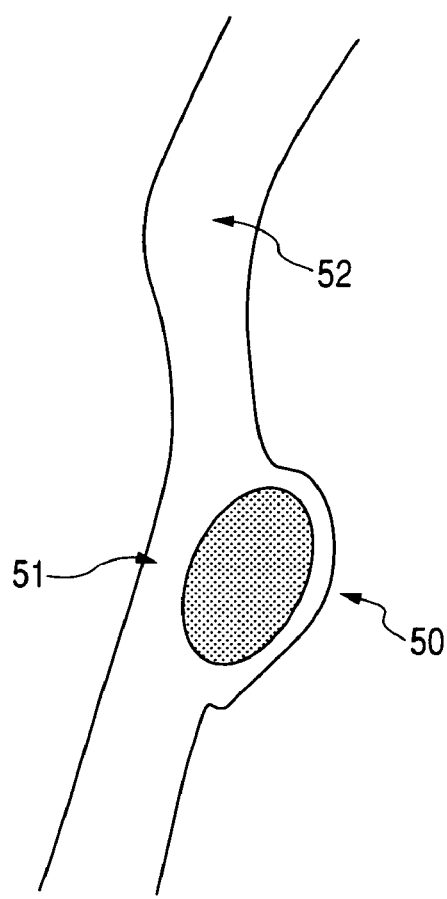
FIGS. 33A and 33B are drawings for illustrating the situation, in an MIP image, of a portion where a bloodstream 52 is obstructed by a calcified region 50 attached inside a blood vessel.
Figure 33B:
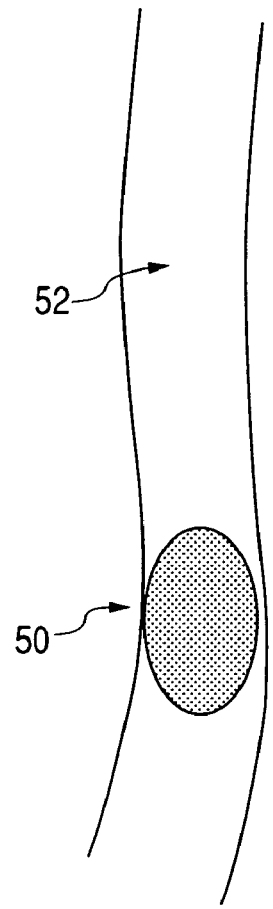
Figure 34:
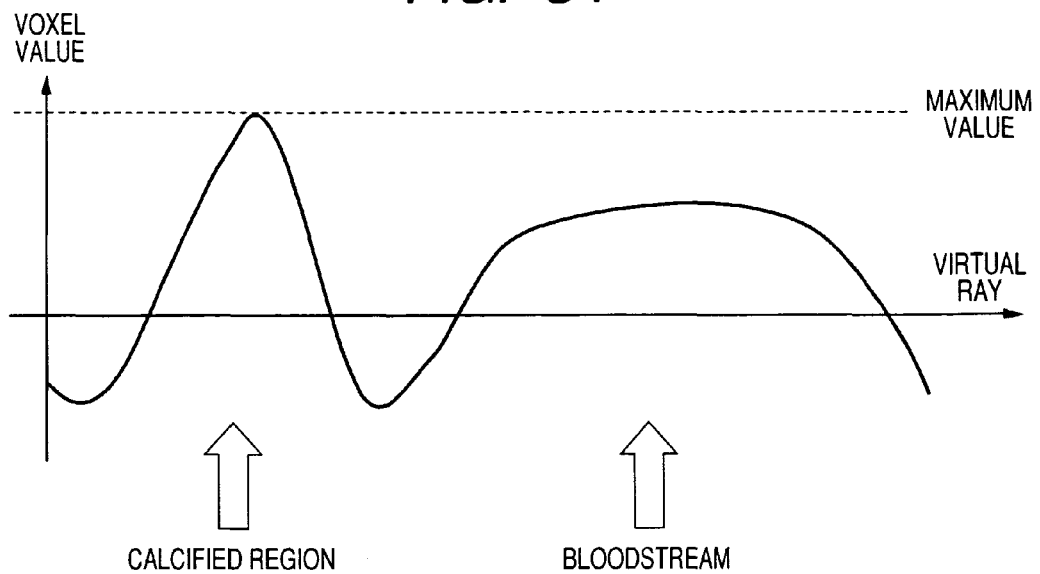
FIG. 34 is a drawing for explaining characteristics of voxel values profile along a virtual ray, showing a change in voxel values on the virtual ray at the portion where a calcified region having a high CT value exists in a blood vessel.
Figure 35:
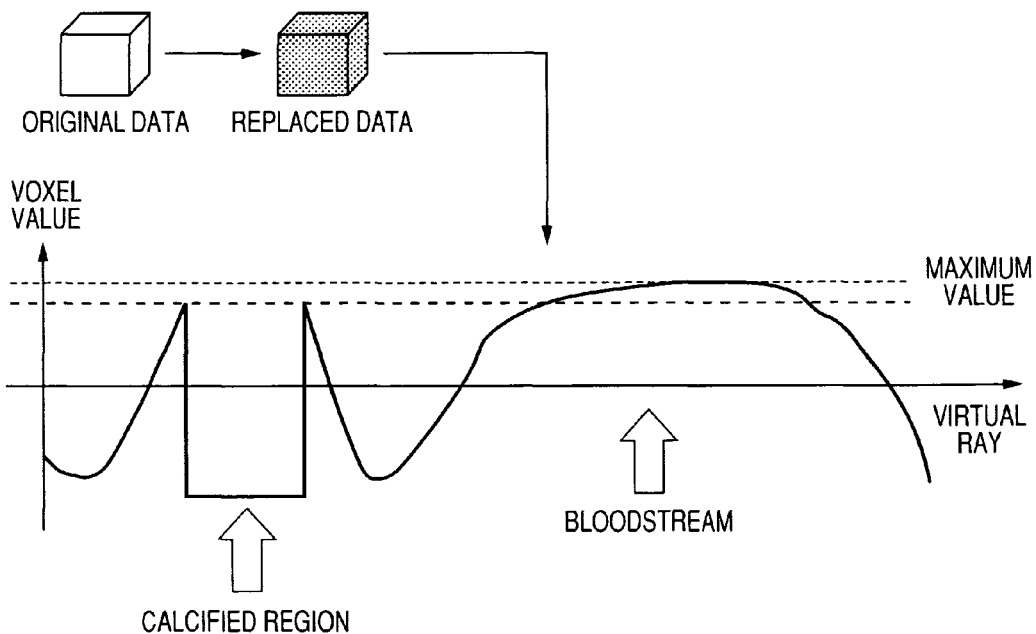
FIG. 35 is a drawing for explaining characteristics of voxel values profile along a virtual ray, illustrating a solution of the related art when the bloodstream positioning at the back of or in front of the calcified region is observed in the MIP image.
Figure 36:
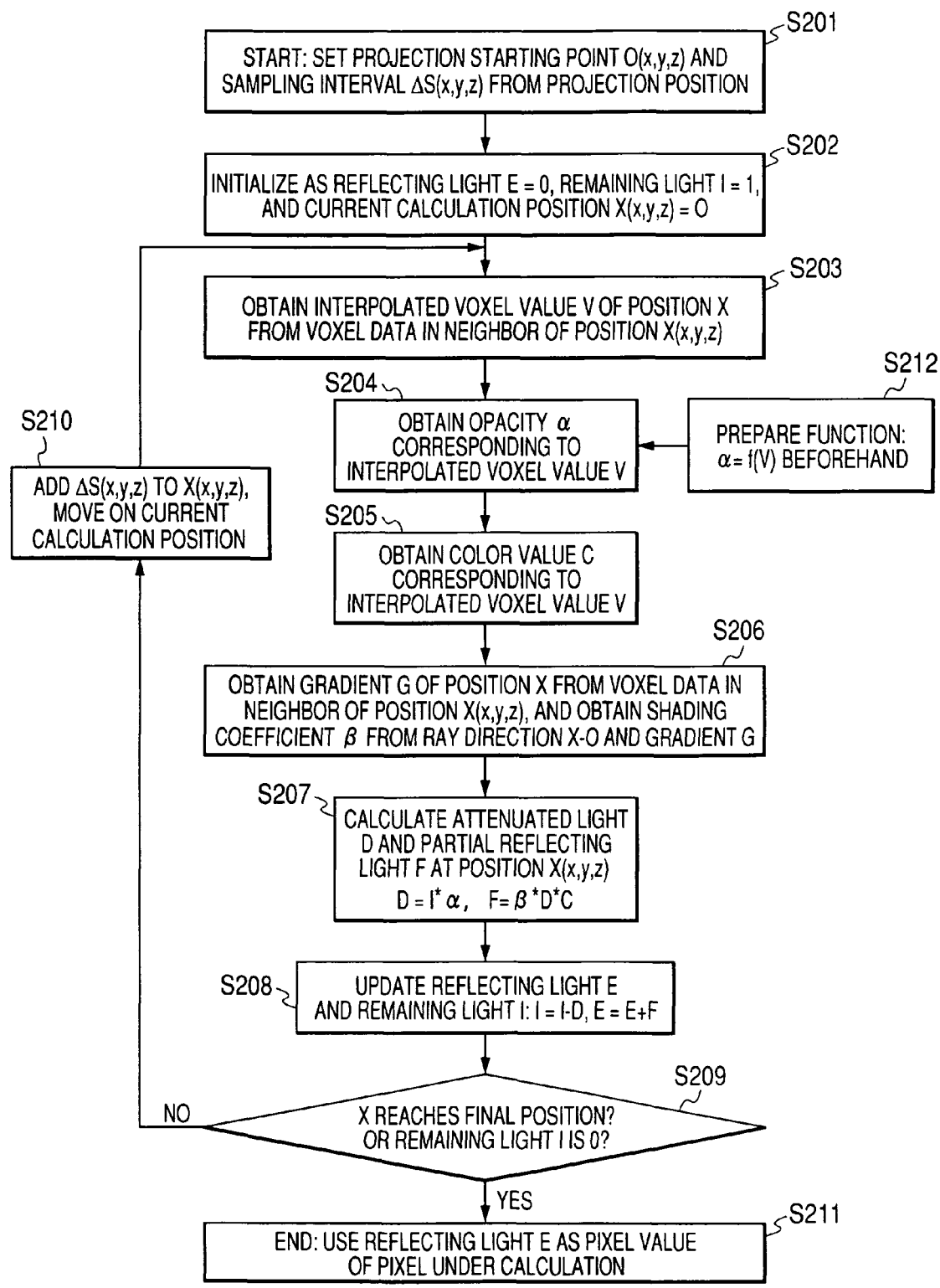
FIG. 36 is a flow chart showing calculation of each pixel on the screen in a ray casting method of the related art.
Figure 37:
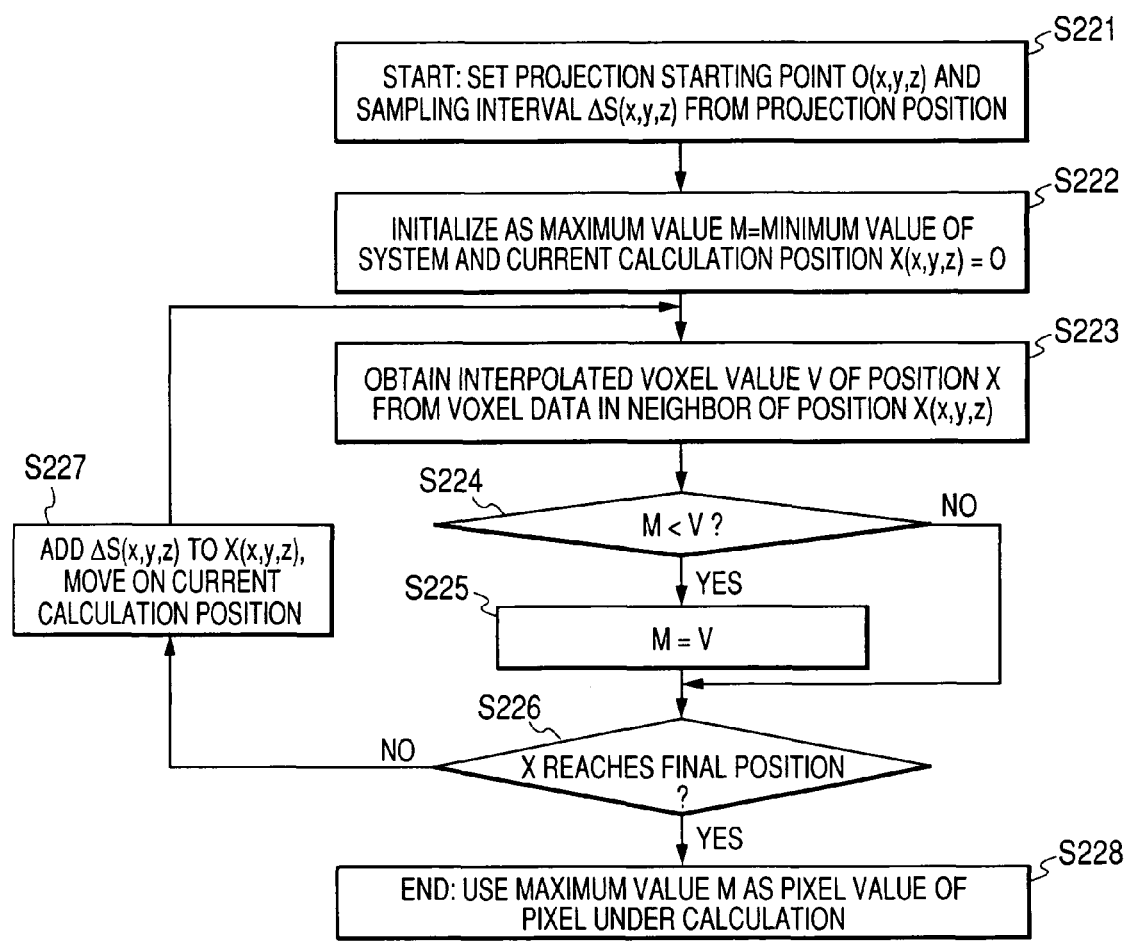
FIG. 37 shows a flow chart for calculating each pixel on the screen in an MIP processing of the related art.
Figures 38A, 38B, 38C:
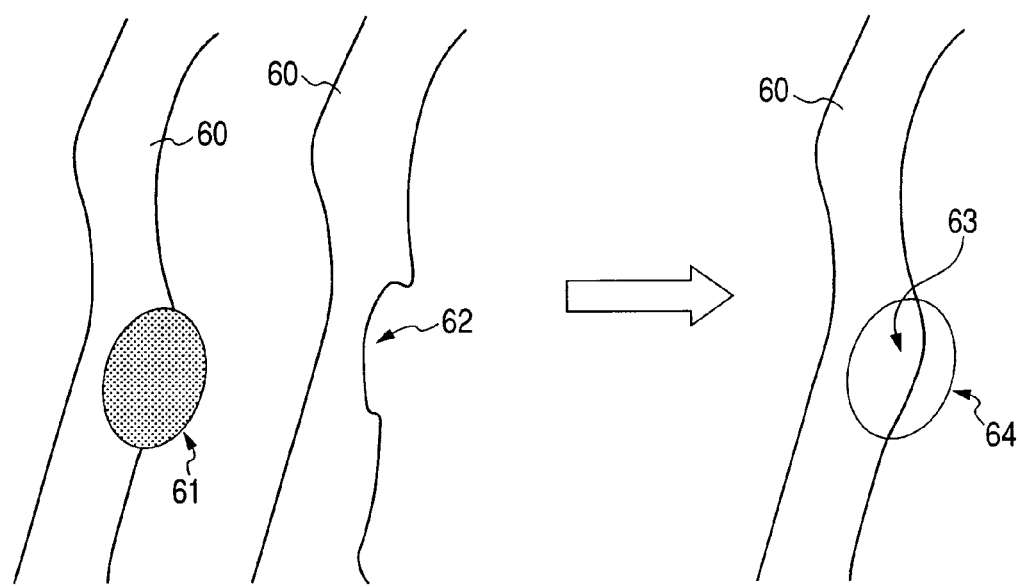
FIGS. 38A, 38B and 38C are drawings for illustrating the problems in the MIP image of the related art.

FIG. 28 shows a flow chart of the case when the opacity is changed using the change in voxel values (Application 2 for ray casting method). This processing is a calculation for each pixel on the screen, and the following calculation is conducted for all the pixels on the image. First, from a projection position, a projection starting point $\underline{O}$(x,y,z) and a sampling interval ΔS(x,y,z) are set (Step S121).

Next, a reflecting light E is initialized as "0", a remaining light I as "1", and a current calculation position X(x,y,z) as "$\underline{O}$" (Step S122). Then, from voxel data in the neighbor of the position X(x,y,z), an interpolated voxel value V of the position X is obtained (Step S123). In addition, an opacity α considering the interpolated voxel value V and "exclusion" is obtained (Step S124). In this case, by α1=f(V), α2=g(X), and α=α1*(1−α2), the exclusion degree of the position X is calculated (Step S132).

Next, a color value C corresponding to the interpolated voxel value V is obtained (Step S125). Then, from voxel data in the neighbor of the position X(x,y,z), a gradient G of the position X is obtained. From a ray direction X−$\underline{O}$ and the gradient G, a shading coefficient β is obtained (Step S126).

Next, an attenuated light D (D=I*α) and a partial reflecting light F (F=β*D*C) at the position X(x,y,z) are calculated (Step S127). Then, the reflecting light E and the remaining light I are updated (I=I−D, E=E+F) (Step S128).

Next, whether X reaches a final position or not, and whether the remaining light I is "0" or not are determined (Step S129). When X is not at the final position and the remaining light I is not "0" (no), ΔS(x,y,z) is added to X(x,y,z), the current calculation position is moved on (Step S130), and the processes of and after Step S123 are repeated.

On the other hand, when X reaches the final position or the remaining light I becomes "0" (yes), the calculation is completed by employing the reflecting light E as a pixel value of the pixel under calculation (Step 131). Thus, by changing the opacity using the change in voxel values, it is possible to display the rim of the calcified region and the bloodstream in front of and at the back of the calcified region without displaying the center part of the calcified region.

Ninth Embodiment (MIP Processing—with Gradient and Flip-Over)

FIG. 29 shows a flow chart of MIP processing in which gradient processing and flip-over processing are conducted. This processing is a calculation for each pixel on the screen, and the following calculation is conducted for all the pixels on the image. First, from a projection position, a projection starting point $\underline{O}$(x,y,z) and a sampling interval ΔS(x,y,z) are set (Step S141).

Next, a maximum value M is initialized as a minimum value of the system, and a current calculation position X(x,y,z) as "$\underline{O}$" (Step S142). An interpolated voxel value V of the position X(x,y,z) is obtained from voxel data in neighbor of the position X (Step S143). Then, voxel data VS1 in neighbor of the position X(x,y,z) is obtained (Step S144), and a flipped-over data VS2 is calculated from VS1 (Step S145).

Next, gradient G at the position X of the flipped-over data VS2 is calculated (Step S146), and an inner product I of ray direction X−$\underline{O}$ and the gradient G is obtained (Step S147). Then, whether the condition of −T<I<T is satisfied or not for a threshold value T is determined (Step S148). When the condition is satisfied (yes), the maximum value M is compared with the interpolated voxel value V (Step S149). When the maximum value M is smaller than the interpolated voxel value V (yes), the interpolated voxel value V is assigned to the maximum value M as a new Maximum value (Step S150).

Next, whether X reaches a final position or not is determined (Step S151). When X is not at the final position (no), ΔS(x,y,z) is added to X(x,y,z), the current calculation position is moved on (Step S152), and the processes of and after Step S143 are repeated. Moreover, when X reaches the final position (yes), the maximum value M is employed as a pixel value of the pixel under calculation, and the processing is completed (Step S153). Thus, by combining the gradient processing and the flip-over processing, it is possible to display the rim of the calcified region and the bloodstream in front of and at the back of the calcified region without displaying the center part of the calcified region.

The image processing method of the embodiments can be conducted by GPU (Graphic Processing Unit). GPU is a processor which is designed to be specialized particularly in image processing as compared with general-purpose CPU. Usually, GPU is mounted on a computer separately from CPU.

Moreover, in the image processing method of the embodiments, calculation of volume rendering can be divided by a certain image region, a region of volume, or the like, and subsequently the divided regions after the calculation can be superimposed on each other. Accordingly, the image processing method of the present embodiment can be performed by parallel processing, network distributed processing, or a combination thereof.

The embodiments of the invention are described in the above, however, the invention is not limited to the above embodiments. The following examples are also applied to the invention.

EXAMPLE 1

For example, a lump having a high contrast in the neighbor of an observation object is referred to as A, and a vector determined by a projection method and a projection direction is referred to as B. Herein, B is a viewing direction in the case of parallel projection, a radial vector in the case of VE (virtual endoscope), or a vector orthogonal to the viewing direction.

In this case, in the rendering processing by ray casting, for the purpose of preventing A from being an obstruction when observing the observing object, the processing has a mechanism that the outline of A is particularly emphasized selectively and dynamically in each step of ray casting. Then, according to the emphasized result and B, any of the following processes is performed: (1) skip the step; (2) replace original data with other values, and process; or (3) change the amount of attenuation in the case of a rendering method wherein attenuation of light is simulated.

EXAMPLE 2

A lump having a high contrast in the neighbor of an observation object is referred to as A, the observation object as B, and a vector determined by a projection method and a projection direction as C. Herein, C is a viewing direction in the case of parallel projection, a radial vector in the case of VE, or a vector orthogonal to the viewing direction.

In this case, in the rendering processing by ray casting, in a situation that A obstructs the observation of B, the processing has a mechanism that the outline of A is particularly emphasized selectively and dynamically in each step of ray casting, for the following purposes: (1) the image of B is not deteriorated in the region where B is not overlapped with A; (2) the region where B overlaps with A is removed from or made translucent in the image, except for a part of the image of A showing the characteristic of A briefly; and (3) the whole view of B can be observed without being obstructing by A. Then, according to the emphasized result and C, any of the following processes is performed: (1) skip the step; (2) replace original data with other values, and process; or (3) change the amount of attenuation in the case of a rendering method wherein attenuation of light is simulated.

EXAMPLE 3

For example, an application to an air image (volume rendering image which is translucent and where only the outline is easily viewable) of a colon is possible. In the case of the air image, "A=B" and "the region showing the characteristic of A briefly=(equals to) the region desired to be observed of B".

In this case, a lump having a high contrast in the neighbor of an observation object is referred to as A, the observation object as B (there is a case that B is identical with A), and a vector determined by a projection method and a projection direction as C. Herein, C is a viewing direction in the case of parallel projection, a radial vector in the case of VE, or a vector orthogonal to the viewing direction.

In this case, in the rendering processing by ray casting, in a situation that A obstructs the observation of B, the processing has a mechanism that the outline of A is particularly emphasized selectively and dynamically in each step of ray casting, for the following purposes: (1) in the region where B is not overlapped with A, the image of B is not deteriorated to hinder the observation of B; (2) the region where B overlaps with A is removed from or made translucent in the image, except for a part of the image of A showing the characteristic of A briefly; and (3) the whole view of B can be observed without being obstructed by A. Then, according to the emphasized result and C, any of the following processes is performed: (1) skip the step; (2) replace original data with other values, and process; or (3) change the amount of attenuation in the case of a rendering method wherein attenuation of light is simulated.

EXAMPLE 4

A lump having a high contrast in the neighbor of an observation object is referred to as A, the observation object as B (there is a case that B is identical with A), and a vector determined by a projection method and a projection direction as C. Herein, C is a viewing direction in the case of parallel projection, a radial vector in the case of VE, or a vector orthogonal to the viewing direction.

In this case, in the rendering processing by ray casting, in a situation that A obstructs the observation of B, the processing has a mechanism that the outline of A is particularly emphasized selectively and dynamically in each step of ray casting, for the following purposes: (1) in the region where B is not overlapped with A, the image of B is not deteriorated to hinder the observation of B; (2) the region where B overlaps with A is removed from or made translucent in the image, except for a part of the image of A showing the characteristic of A briefly; and (3) the whole view of B can be observed without being obstructed by A. Then, when the emphasized result and C satisfy a certain condition which is set beforehand, any of the following processes is performed as an alternative to usual processing: (1) skip the step; (2) replace original data with other values, and perform usual processing; (3) perform processing to which a transformation with the emphasized result and C is added as a preprocessing of usual processing; or (4) change the amount of attenuation in the case of a rendering method wherein attenuation of light is simulated.

EXAMPLE 5

In the above examples, it is assumed that the outline of A is left in the result image. However, an embodiment in which the outline of A is not left is also possible. In this case, a lump having a high contrast in the neighbor of an observation object is referred to as A, the observation object as B (there is a case that B is identical with A), and a vector determined by a projection method and a projection direction as C. Herein, C is a viewing direction in the case of parallel projection, a radial vector in the case of VE, or a vector orthogonal to the viewing direction.

In this case, in the rendering processing by ray casting, in a situation that A obstructs the observation of B, the processing has a mechanism that the outline of A is particularly emphasized selectively and dynamically in each step of ray casting, for the following purposes: (1) in the region where B is not overlapped with A, the image of B is not deteriorated to hinder the observation of B; (2) in the region where B overlaps with A, (2.1) regions other than a part of the projection image of A showing the characteristic of A briefly or (2.2) all of the projection image of A, is removed from or made translucent in the image; (3) the whole view of B can be observed without being obstructed by A. Then, when "the original data, the emphasized result and C" at the position in process of each step of ray casting and in the neighbor the position satisfy a certain condition which is set beforehand, any of the following processes is performed as an alternative to usual processing: (1) skip the step; (2) replace original data with other values, and perform usual processing; (3) perform processing to which a transformation with the emphasized result and C is added as a preprocessing of usual processing; or (4) change the amount of attenuation in the case of a rendering method wherein attenuation of light is simulated.

EXAMPLE 6

The image processing method of the invention comprises (A) in volume rendering, (B) determining whether the value of a sample point of an observation object is employed or not (excluded or not) in each sample point on the virtual ray. In this example, (C) an object of the invention is to render only the outline of an obstructing region. Moreover, (D) it is desirable to use data generated from volume data for determination of exclusion (this is not indispensable).

In related arts, an obstructing region is removed by modifying a volume or generating a mask volume. In the invention, an obstructing region is dynamically calculated at the time when the virtual ray is projected. Accordingly, an image in which the projection direction is considered can be generated (extraction of the outline from the direction of the viewpoint). Therefore, since the display of the outline changes as the direction of the viewpoint is changed, a desirable image is easily obtained.

(A) The image processing method of the invention can be used in general volume rendering, and is effectively utilized particularly in MIP method and ray casting method. In volume rendering, there are methods such as (A1) MIP method and MinIP method, represented by MIP method, wherein one sample point is selected from the data on the virtual ray to determine a pixel. Furthermore, there are methods such as (A2) ray casting method, Raysum method and average value method, represented by ray casting method, wherein a plurality of sample points on the virtual ray are selected to determine a pixel.

The present invention can be applied to any of the methods. In (A1), the present method can be implemented by, after (B), excluding the sample points selected in (B) from the data on the virtual ray (an implementation example in MIP method). On the other hand, in (A2), the present method can be implemented by, after (B), excluding the sample points selected in (B) from the plurality of points on the virtual ray.

Moreover, in the method of (A2) such as ray casting method, though (A), (B) and (C) can be implemented as they are as described above, the sample points are not necessarily excluded, and the degree of contribution on the determination of pixels can be lowered.

For example, in ray casting method, an opacity α is calculated based on voxel values for sample points through which the virtual ray passes. The value of opacity α can be manipulated for the sample points selected in (B).

(B) In the image processing method of the invention, it is determined whether the value of a sample point of an observation object is employed or not (excluded or not) in each sample point on the virtual ray For the determination of exclusion, in addition to the above method (B1) using gradient (note: for flipped-over data, gradient may be calculated for all the sample points or for a part thereof (such as in the neighbor of the threshold value)) and the method (B2) using a change such as a difference of voxel values, following methods can be used: (a) excluding high-frequency components through frequency analysis; (b) calculating variance of data and excluding sample points having the variance equal to or larger than a threshold value; (c) using a noise removal filter; and the like. Moreover, the exclusion may be determined by not only binary values of "exclude" and "not exclude" but also multiple values with an "exclusion degree".

(C) In the image processing method of the invention, an object of the invention is to render only the outline of an obstructing region. In addition, two-dimensional characteristics of data can be displayed, not being limited to the outline. Moreover, by dynamically performing calculation for the exclusion irrespective of the outline, it is possible to generate a new image in medical imaging.

(D) Moreover, in the image processing method of the invention, it is desirable to use data generated from volume data for determination of exclusion (this is not indispensable). Here, following cases are considered: (D1) flipped-over data is used; (D2) data below a threshold vale is used (when gradient is used); (D3) When gradient is used, the same effect can be obtained without flip-over by determining (1) to exclude when a voxel value is considerably larger than a threshold value, (2) to exclude according to gradient when a voxel value is close to the threshold value, and (3) not to exclude when a voxel value is considerably smaller than the threshold value;

(D4) mask data is used, that is, the same effect can be obtained by calculating gradient on the mask data; and (D5) data generated from the volume data may be (a) calculated at the time when a virtual ray is projected, or (b) generated as second volume data beforehand.

In the above embodiments, determination of a calcified region is conducted. However, this invention may be applied to the determination of any region as long as it is an obstructing region. For example, it is particularly effective for observation of medical devices such as stents, medical clips, and medical coils, which are inserted in a human body. Moreover, the region may be a region of bloodstream or an organ. Furthermore, the region may be a contrast region where signals are emphasized by a contrast agent. The contrast region includes a contrast region by a low concentration contrasting. In addition, the obstructing region in not limited to a high-signal region, and may be a low-signal region such as an air bubble so that a two-dimensional outline thereof can be displayed. Moreover, the obstructing region may be a region having medium signal intensity such as fat so that a two-dimensional outline thereof can be displayed.

In the above embodiments, the obstructing region is a lump region. However, the region may be of any form as long as it is an obstructing region. For example, in an image in which bloodstreams having different circumferences are intricately crossed with each other as shown in FIG. 30A, the bloodstreams can be accurately recognized by displaying the two-dimensional outline of the bloodstreams as shown in FIG. 30B. Moreover, in the case of radiographic contrast of intestines, the positional relationship and the shape of the intestinal wall folded intricately can be well recognized by displaying the two-dimensional outline of the intestines.

In the above embodiments, the image according to the invention is solely displayed but the image according to the invention may be displayed in combination with the other images. For example, the image according to the invention and the image generated by the related art may be displayed together being side by side or overlapped. In this case, the images by the same angle of view, parallel projection method, perspective projection method, or cylindrical projection method, and data on the virtual ray may be obtained at once or sequentially according to the necessity of calculation.

In the above embodiments, the whole image is generated by the same calculation method. However, the image processing according to the present method may be applied to only a part of the image. For example, the image processing according to the present method may be applied to only the neighbor of a pointer by a pointing device such as a mouse. Thereby, it becomes easy to observe the image while comparing the image processing according to the related art and the image processing according to the present method.

In the above embodiments, the whole image is generated by the same calculation method. However, the image processing according to the present method may be applied to only a part of the image. Particularly in the present method, for the portion where an obstructing region does not exist, the same image can be obtained as that obtained in the method of the related art. Thus, the processing speed can be increased by generating an image by the method of the related art beforehand, and determining particularly the region which includes an obstructing region automatically. In particular, in the example using MIP method, the present method can be applied only to the portion where a maximum value on the virtual ray is equal to or larger than a threshold value.

In the above embodiments, gradient information is obtained by acquiring the difference of neighboring 3×3×3 voxel region of a target voxel. However, the method for obtaining the gradient information is not limited to the above example. For example, in the case when the value of a point through which the virtual ray passes is obtained by not the target voxel but interpolation of neighboring voxels, the neighboring 3×3×3 voxel region of the target voxel may be also obtained by interpolation, respectively. Moreover, not the 3×3×3 voxel region but a 2×2×2 voxel region may be used. Furthermore, the gradient may be obtained after normalizing the voxel in the direction of the virtual ray.

In the above embodiments, since it is difficult to intuitively understand the degree of contribution of a voxel on the virtual ray to an image, it is possible to display an image in which the degree of contribution of the voxel contained in volume data is separately visualized. For example, it is possible to display a graph which shows the degree of contribution of a voxel on the virtual ray. Moreover, a graph can be displayed which shows the degree of contribution for a plurality of virtual rays. For example, a CPR (curved multi planar reconstruction) image is generated using planes composed of a group of virtual rays corresponding to a line on the image, and the degree of contribution of a voxel on a virtual ray relating to each point on the CPR image can be mapped while superimposed.

In the above embodiments, since it is difficult to intuitively understand whether a voxel on the virtual ray is used or excluded (not used) in the calculation of an image, it is possible to display an image in which whether the voxel contained in the volume data is used or excluded in the generating the image is separately visualized. For example, it is possible to display a graph which shows whether a voxel on the virtual ray is used or excluded in generating an image. Moreover, a graph can be displayed which shows whether a voxel on the virtual ray is used or excluded in generating an image for a plurality of virtual rays. For example, a CPR (curved multi planar reconstruction) image is generated using planes composed of a group of virtual rays corresponding to a line on the image, and whether a voxel on a virtual ray relating to each point on the CPR image is used or excluded in generating an image can be mapped while superimposed.

In the above embodiments, since it is difficult to intuitively understand how a profile pattern on the virtual ray is replaced, the replaced profile pattern on the virtual ray may be displayed. For example, it is possible to display the replaced profile pattern corresponding to a point pointed by a pointing device, in a same window by being superimposed on the image generated by the present method, or in another window. Moreover, original profile pattern can be also displayed being superimposed to the replaced profile pattern.

In the above embodiments, particularly in the image processing method using only a single point on a virtual ray, since it is difficult to intuitively understand the three-dimensional position where the single point is obtained, the three-dimensional position where the single point is obtained can be visualized. For example, an image is generated in which the three-dimensional position where the single point is obtained is mapped as depth information. Moreover, the mapped image can be displayed by being superimposed on or arranged side by side with an image generated by the present method or a calculation method of the related art.

In the above embodiments, calculation is conducted by a single processing unit. However, parallel processing may be conducted by a plurality of processing units. For example, in the present method, since calculation can be conducted independently for each virtual ray, the calculation can be conducted for each virtual ray in parallel.

In the above embodiments, the image processing is conducted by a single central processing unit. However, GPU (graphics processing unit) equipped with a programmable shader may be used for the image processing. Moreover, the other processing units may be employed.

In the above embodiments, parameters used in the image processing are predetermined beforehand. However, the parameters may be dynamically changed according to the operation of a user. For example, a threshold value for flip-over processing may be changed by operating a slider set on the screen.

In the above embodiments, a direction vector of the virtual ray is used. However, other direction vectors may be employed. For example, by using a direction vector which crosses with the direction of the virtual ray obliquely, an effect corresponding to shades can be expressed in the image generated through MIP processing and the like. Moreover, for example, by using the direction vector of a central line of a blood vessel, the region in front of the blood vessel and the region at the back of the blood vessel are displayed differently.

In the above embodiments, MIP method is used as a volume rendering method wherein values of at least one point of data on the virtual ray are used in determining the pixel values, and positional relationship of the at least one point is mutually exchangeable. However, other methods may be employed for the volume rendering method. For example, a MinIP (minimum intensity projection) method wherein a minimum value is used may be employed. Moreover, for example, an average value method wherein an average value of at least one point is used may be also employed. Furthermore, for example, a Raysum method wherein a sum of at least one point is used may be employed. Furthermore, for example, a Top10MIP method may be employed wherein values of top ten points on the virtual ray are obtained and an average value thereof is used.

In the above embodiments, gradient at each position in a volume is used. It may be possible to use gradient at a position which is moved from a passing point of the virtual ray in the volume. Thereby, the position on which a two-dimensional outline is rendered deviates, and hence more precise observation is enabled on the boundary region while suggesting the presence of the two-dimensional outline to a user.

In the above embodiments, gradient at each position in a volume is used. It may be possible to use gradient information at a position in a volume other than the volume which is used in determining the pixels. For example, by using other volume data which is different in time series, movement of the two-dimensional outline can be rendered. Moreover, for example, when a mask volume generated beforehand is used, outline information generated by an outline extraction algorithm or a user can be rendered.

In the above embodiments, a still image is generated, but a moving image may also be generated. Moreover, a moving image displayed according to the operation by a user may be dynamically generated. For example, when a moving image wherein a viewpoint rotates around an observation object is first generated, the two-dimensional outline of the observation object can be more precisely observed. Furthermore, for example, in the case when a moving image is used wherein parameters relating to the image processing are changed, the two-dimensional outline can be also more precisely observed.

In the above embodiments, a two-dimensional outline of an observation object is displayed, but the display of the observation object is not limited to the two-dimensional outline. For example, when a portion where the angle between the direction vector of the virtual ray and the gradient vector is small is not excluded but a portion where the angle is large is excluded, the center part of the observation object is emphasized. Moreover, for example, when the determination is performed by the direction of the outer product vector of the direction vector of the virtual ray and the gradient vector, those directing to a specific direction can be displayed among the two-dimensional outlines.

In the above embodiments, opacity is set when ray casting method is used, but any degree of contribution on an image can be set without limiting to opacity. For example, in the average value method, an image can be generated by setting the degree of contribution and using a weighted average instead of the average value.

In the above embodiments, a two-dimensional outline of a calcified region is displayed, but objects to be displayed are not limited to a calcified region. For example, it is particularly effective for observation of medical devices such as stents, medical clips and medical coils, which are inserted in a human body. Moreover, without limiting to a high-signal region, a two-dimensional outline of a low-signal region such as an air bubble may be displayed.

In the above embodiments, volume data obtained from a CT apparatus is used, but the volume data may be obtained by any method or apparatus. For example, volume data obtained from an MRI (magnetic resonance imaging) apparatus or a PET (positron emission tomography) apparatus may be used. Moreover, volume data modified by applying a filtering process or the like to the volume data, or volume data obtained by combining a plurality of volume data may be also employed.

In the above embodiments, the angle between the first vector information and the second vector information is calculated, but the angle may be a negative value or may be larger than 90 degrees. Thereby, only a wall at a front side can be displayed.

The present invention is applicable to an image processing method capable of rendering an image by removing an obstructing region such as a calcified region and determining the outline of the obstructing region dynamically, during calculation of a medical image such as MIP processing.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An image processing method by volume rendering, said image processing method comprising:
    providing at least one processor;
    selecting at least one point which is aligned on a virtual ray; and
    determining a pixel value of an image by the volume rendering based on each value of the selected at least one point,
    wherein said at least one point is selected based on a first vector information and a second vector information, and wherein the second vector information is information about candidates of said at least one point, and
    positional relationship of said at least one point is mutually exchangeable on the virtual ray with another point having a different position on the virtual ray than said at least one point, in determining the pixel value,
    wherein the steps of selecting and determining are executed by the at least one processor.

2. The image processing method according to claim 1, wherein the first vector information is a direction vector of the virtual ray.

3. The image processing method according to claim 1, wherein the second vector information is gradient information.

4. The image processing method according to claim 1, wherein a number of the selected point is one.

5. The image processing method according to claim 1, wherein said at least one point is selected further based on data obtained by replacing original data on the virtual ray.

6. The image processing method according to claim 5, wherein values of the replaced data are obtained by flipping values of the original data over at a threshold value.

7. The image processing method according to claim 1, wherein said at least one point is selected further based on a magnitude of the second vector information.

8. The image processing method according to claim 1, wherein said at least one point is selected further based on an angle between the first vector information and the second vector information.

9. The image processing method according to claim 1, further comprising:
    displaying a two-dimensional outline of a region included in a rendering object on the volume rendering image.

10. The image processing method according to claim 1, wherein the volume rendering image and an another image are displayed arranged in side by side, being overlapped with each other, or by showing a difference of the images.

11. The image processing method according to claim 1, wherein the pixel value is determined only for a region which is designated by a user.

12. The image processing method according to claim 1, wherein the pixel value is determined only for a window provided on a screen.

13. The image processing method according to claim 9, wherein the outline is displayed while continuously changed.

14. The image processing method according to claim 1, wherein the image processing is performed by parallel processing.

15. The image processing method according to claim 1, wherein the image processing is performed by a GPU (graphics processing unit).

16. The image processing method according to claim 1, wherein the image processing is performed by a GUI (graphical user interface) in which parameters are changeable.

17. The image processing method according to claim 1, wherein the image processing is performed by MIP (Maximum Intensity Projection) method, MinIP (Minimum Intensity Projection) method, Raysum method or an average value method.

18. The image processing method according to claim 1, further comprising:
    displaying the selected at least one point on a sectional image of a rendering object, said sectional image including the virtual ray.

19. A non-transitory computer readable medium having a program including instructions for permitting a computer to perform an image processing by volume rendering, said instructions comprising:
    selecting at least one point which is aligned on a virtual ray; and
    determining a pixel value of an image by the volume rendering based on each value of the selected at least one point,
    wherein said at least one point is selected based on a first vector information and a second vector information, and wherein the second vector information is information about candidates of said at least one point, and
    positional relationship of said at least one point is mutually exchangeable on the virtual ray with another point having a different position on the virtual ray than said at least one point, in determining the pixel value.

20. An image processing device for displaying a volume rendering image, said image processing device comprising:
    at least one processor, wherein the image processing device is operative to:
    select at least one point which is aligned on a virtual ray, wherein said at least one point is selected based on a first vector information and a second vector information, and wherein the second vector information is information about candidates of said at least one point;
    determine a pixel value of an image by the volume rendering based on each value of the selected at least one point; and
    display a two-dimensional outline of a region included in a rendering object on the volume rendering image,
    wherein positional relationship of said at least one point is mutually exchangeable on the virtual ray with another point having a different position on the virtual ray than said at least one point, in determining the pixel value.

* * * * *